United States Patent
Nishtala et al.

(10) Patent No.: US 6,616,678 B2
(45) Date of Patent: Sep. 9, 2003

(54) DILATION SYSTEMS AND RELATED METHODS

(75) Inventors: Srinivas Nishtala, Bloomington, IN (US); Stéphane Gobron, Gosport, IN (US); Jeff Smith, Poland, IN (US); Tim Ward, Elletsville, IN (US)

(73) Assignee: SciMed Life Systems, Inc., Maple, MN (US)

( * ) Notice: Subject to any disclaimer, the term of this patent is extended or adjusted under 35 U.S.C. 154(b) by 0 days.

(21) Appl. No.: 09/814,643

(22) Filed: Mar. 22, 2001

(65) Prior Publication Data

US 2001/0012950 A1 Aug. 9, 2001

Related U.S. Application Data

(62) Division of application No. 09/164,001, filed on Sep. 30, 1998.
(60) Provisional application No. 60/087,294, filed on May 29, 1998, and provisional application No. 60/060,217, filed on Oct. 1, 1997.

(51) Int. Cl.⁷ ............................................. A61M 29/00
(52) U.S. Cl. ..................... 606/198; 606/191; 604/104
(58) Field of Search ..................... 616/1, 108, 191–200; 604/96.01–109; 600/201, 204, 207

(56) References Cited

U.S. PATENT DOCUMENTS

| | | | |
|---|---|---|---|
| 3,557,794 A | | 1/1971 | Van Patten |
| 3,568,659 A | * | 3/1971 | Karnegis ..................... 604/105 |
| 4,572,186 A | * | 2/1986 | Gould et al. ................ 604/105 |
| 4,899,729 A | | 2/1990 | Gill et al. |
| 4,906,241 A | | 3/1990 | Noddin et al. |
| 4,921,479 A | | 5/1990 | Grayzel |
| 5,007,926 A | | 4/1991 | Derbyshire |
| 5,139,511 A | | 8/1992 | Gill et al. |
| 5,141,494 A | | 8/1992 | Danforth et al. |
| 5,183,464 A | | 2/1993 | Dubrul et al. |
| 5,217,474 A | | 6/1993 | Zacca et al. |
| 5,246,424 A | | 9/1993 | Wilk |
| 5,275,611 A | | 1/1994 | Behl |
| 5,304,120 A | | 4/1994 | Crandell et al. |
| 5,306,286 A | | 4/1994 | Stack et al. |
| 5,312,360 A | | 5/1994 | Behl |
| 5,318,588 A | | 6/1994 | Horzewski et al. |
| 5,342,305 A | | 8/1994 | Shonk |
| 5,431,676 A | | 7/1995 | Dubrul et al. |
| 5,447,503 A | | 9/1995 | Miller |
| 5,454,790 A | | 10/1995 | Dubrul |
| 5,456,667 A | | 10/1995 | Ham et al. |
| 5,470,313 A | | 11/1995 | Crocker et al. |
| 5,476,505 A | | 12/1995 | Limon |
| 5,505,699 A | | 4/1996 | Forman et al. |
| 5,540,713 A | | 7/1996 | Schnepp-Pesch et al. |
| 5,562,620 A | | 10/1996 | Klein et al. |
| 5,618,299 A | | 4/1997 | Khosravi et al. |
| 5,618,300 A | * | 4/1997 | Marin et al. ................ 604/106 |
| 5,713,907 A | | 2/1998 | Hogendijk et al. |
| 5,824,054 A | | 10/1998 | Khosravi et al. |
| 5,868,708 A | * | 2/1999 | Hart et al. .................. 604/107 |
| 5,868,779 A | * | 2/1999 | Ruiz ........................... 606/194 |

FOREIGN PATENT DOCUMENTS

| | | |
|---|---|---|
| EP | 368473 A2 | 5/1990 |
| GB | 2275421 A | 8/1994 |
| WO | WO91/12846 | 9/1991 |
| WO | WO97/43958 | 11/1997 |

* cited by examiner

*Primary Examiner*—Glenn K. Dawson
(74) *Attorney, Agent, or Firm*—Testa, Hurwitz & Thibeault, LLP

(57) ABSTRACT

Devices and methods permit dilation of a track of a body to any of a plurality of diameters using a single integrated device that can reach any of a plurality of expanded diameters upon actuation by a user of an actuating mechanism which directs and controls the dilation of a dilating element to which it is connected by a dial and transmission mechanism. A variety of dials, transmission mechanisms and dilating elements are disclosed which may be combined in a variety of ways.

14 Claims, 32 Drawing Sheets

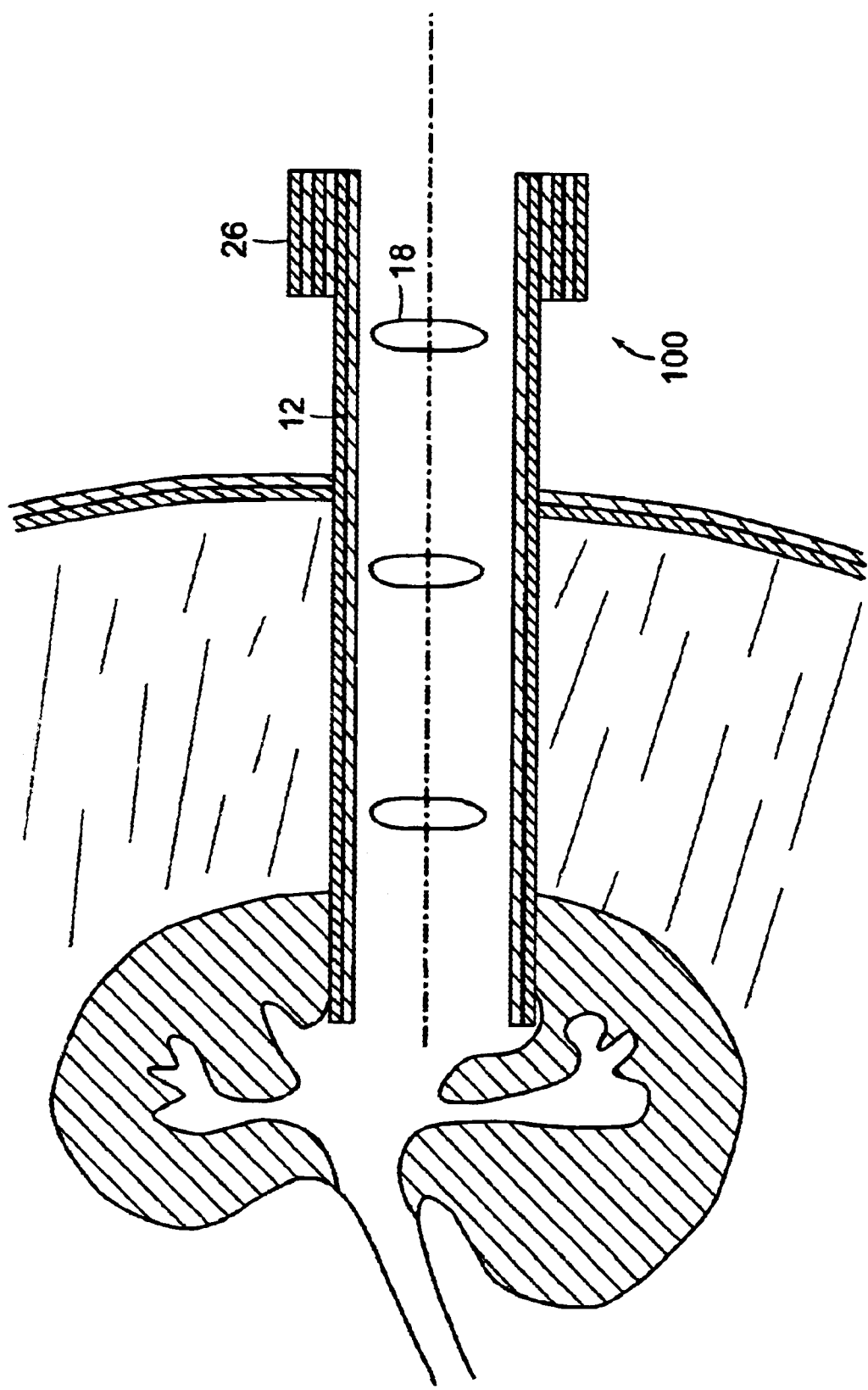

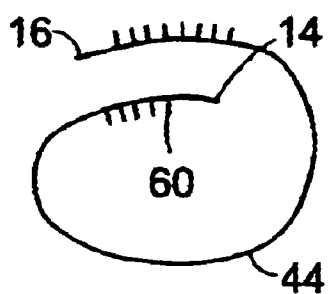
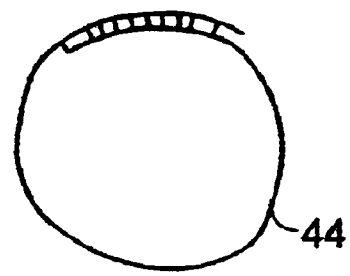
FIG. 4C          FIG. 4D
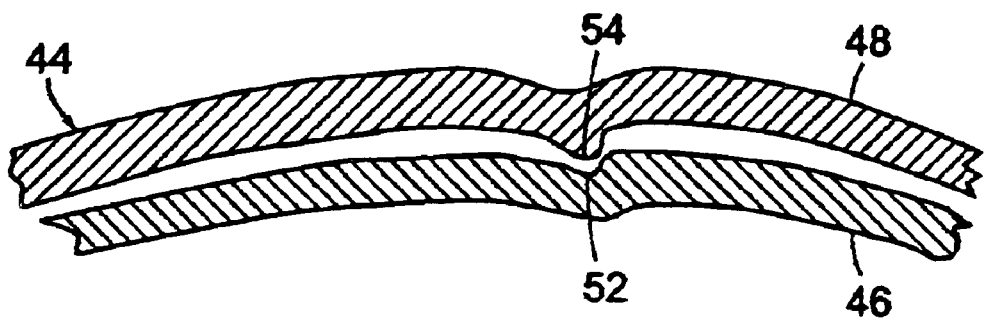
FIG. 4E
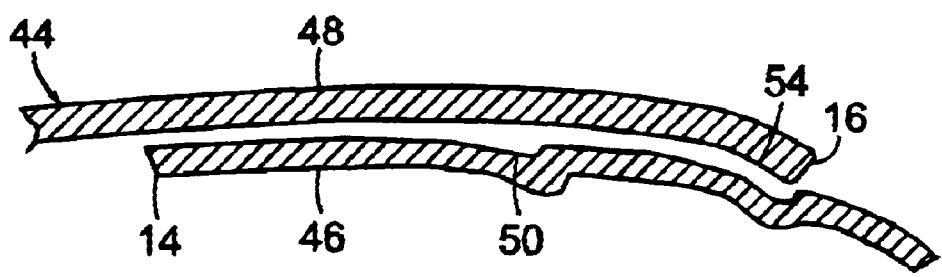
FIG. 4F

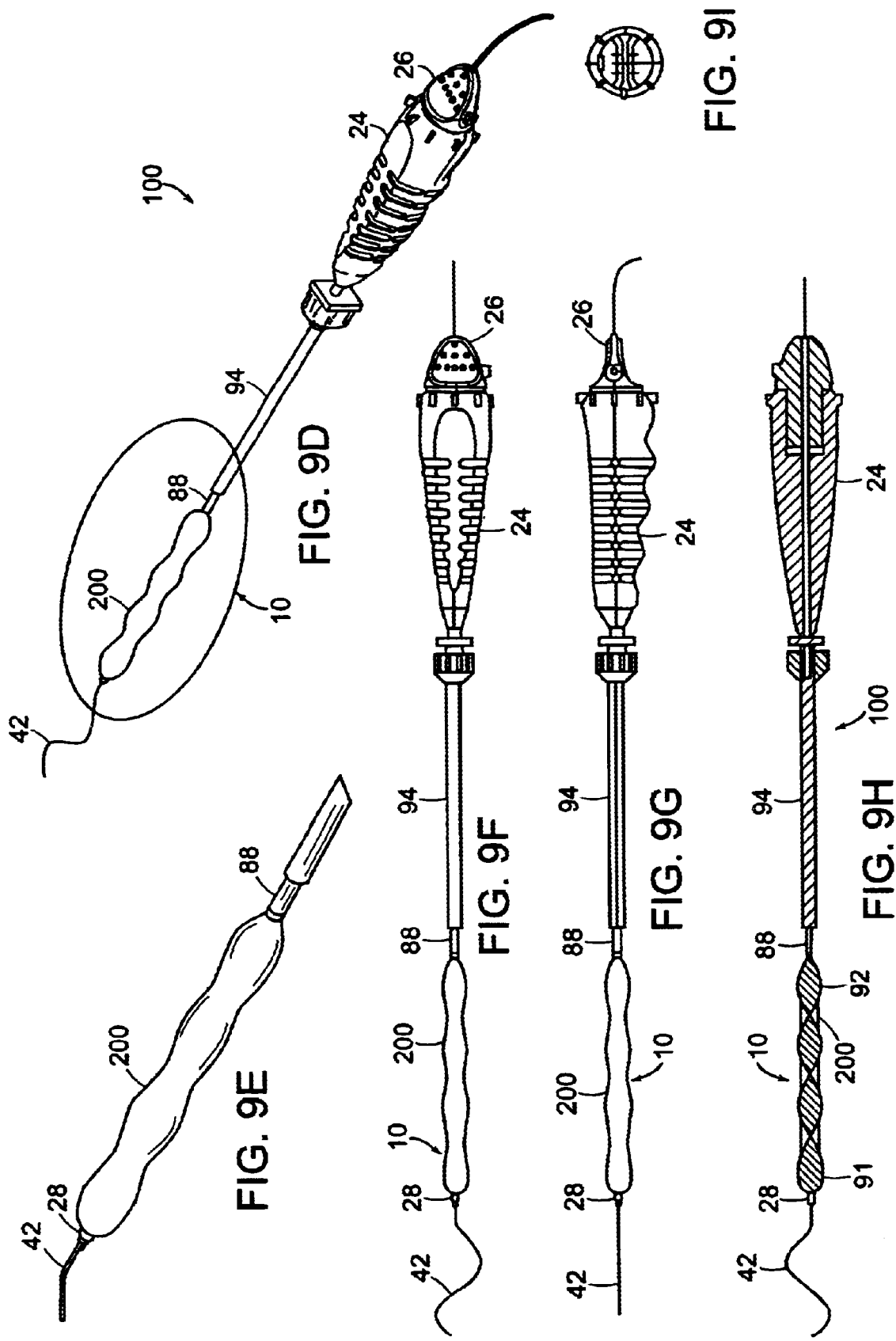

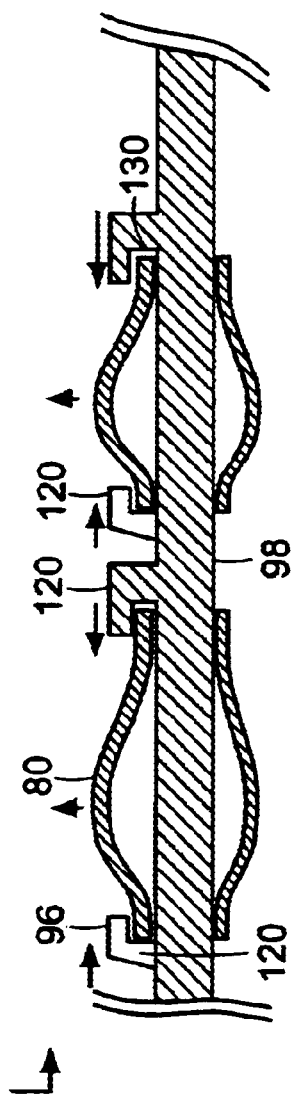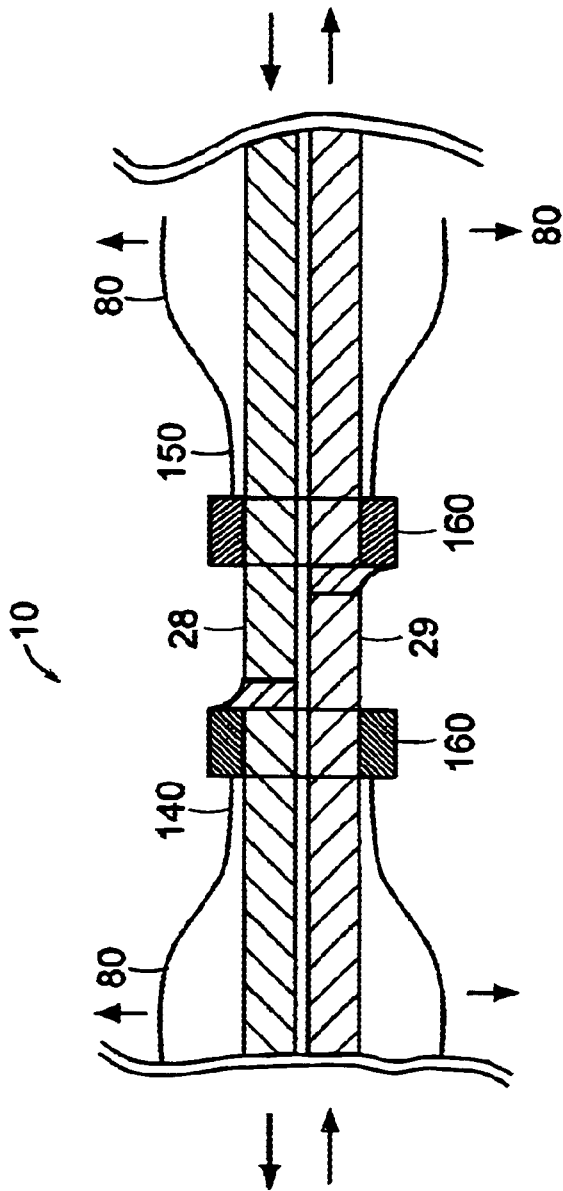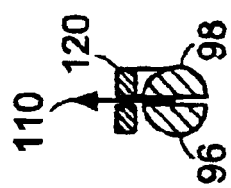

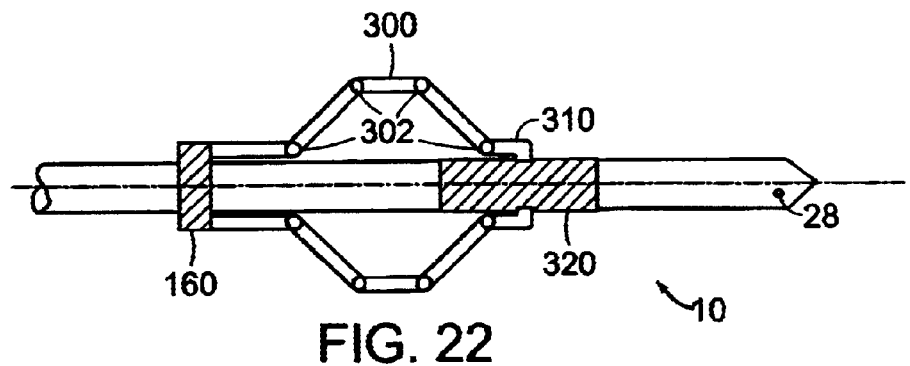
FIG. 22
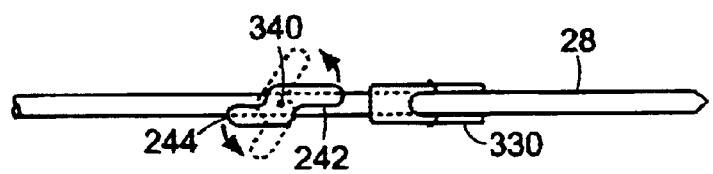
FIG. 23A
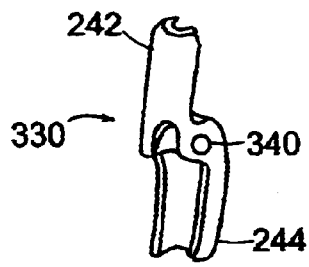
FIG. 23B
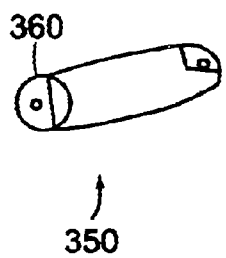
FIG. 24A
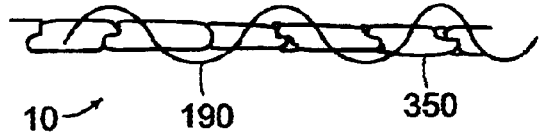
FIG. 24B
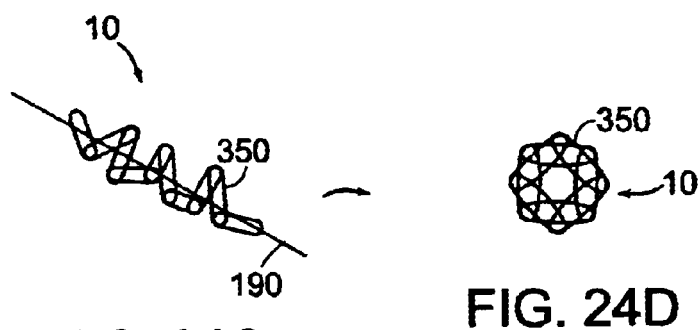
FIG. 24C
FIG. 24D

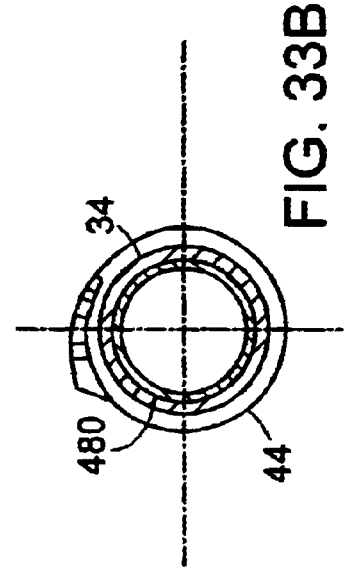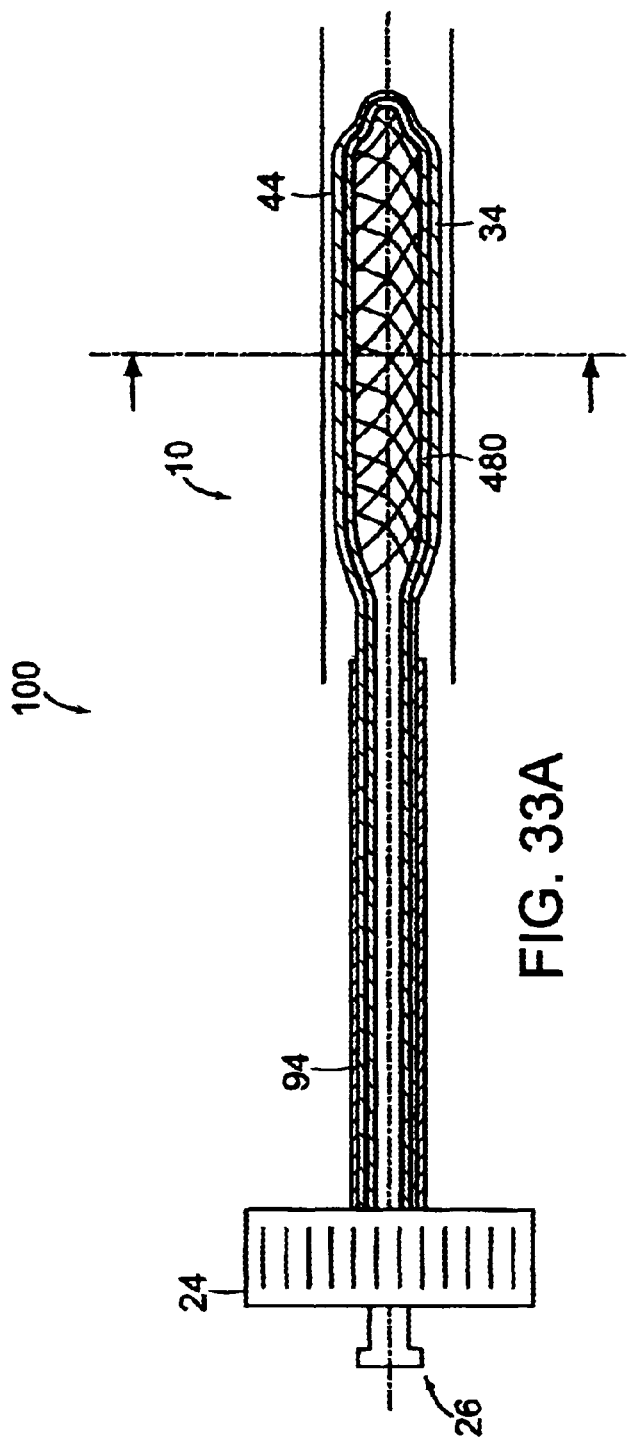

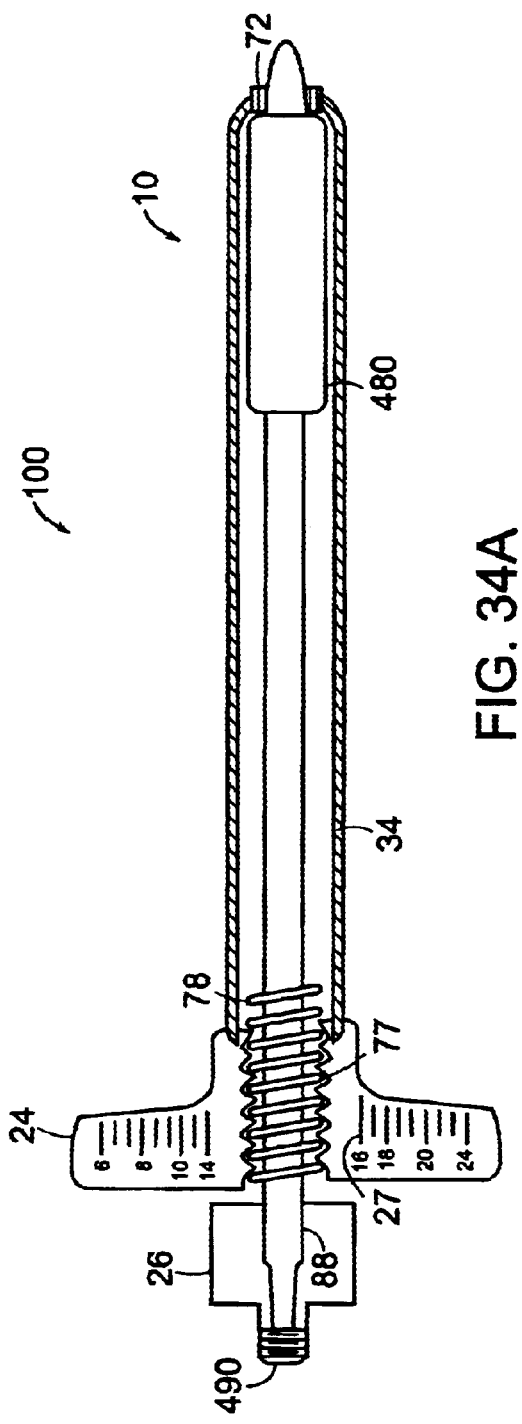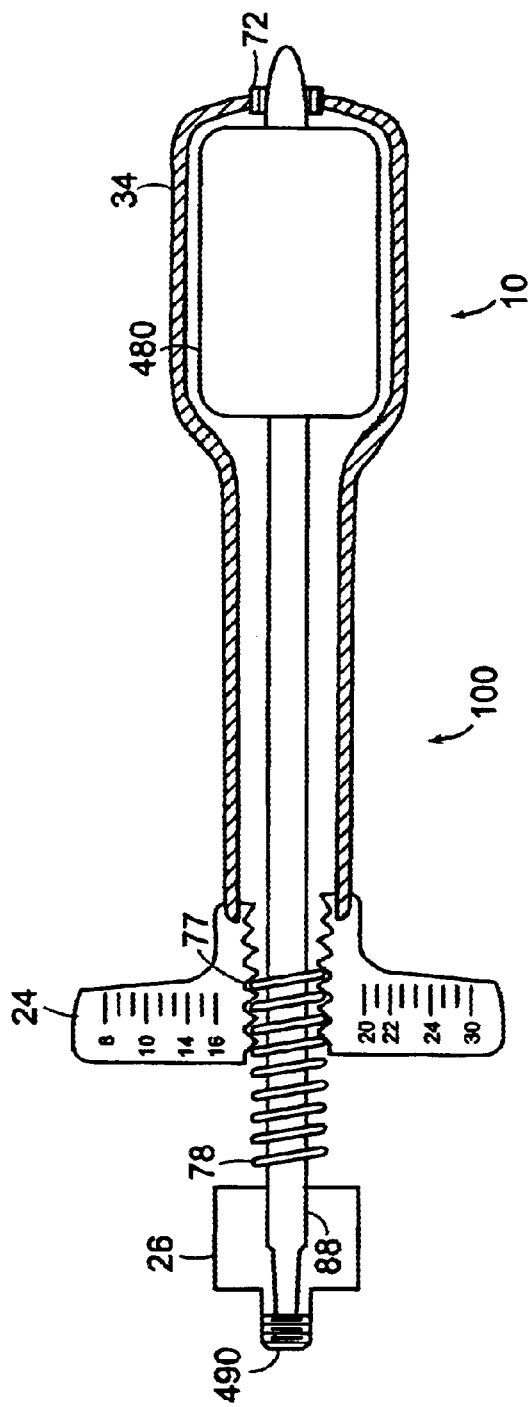
FIG. 34A
FIG. 34B

DILATION SYSTEMS AND RELATED METHODS

CROSS-REFERENCE TO RELATED APPLICATIONS

This application is a divisional application of application Ser. No. 09/164,001 filed on Sep. 30, 1998, now abandoned, which claims the priority to and the benefit of U.S. provisional patent application serial numbers 60/060,217 and 60/087,294 filed on Oct. 1, 1997 and May 29, 1998 respectively which are incorporated herein by reference in their entirety.

TECHNICAL FIELD

The present invention generally relates to dilation systems and related methods of their use. The systems and methods are for gaining access to portions of a patient's body by a physician, for example to obtain percutaneous access to the kidney by a urologist or a radiologist for nephrolithotomy. In particular, the present invention relates to dilation systems throughout the length of the opening and methods for dilating a track opening to a desired size and maintaining that opening with a single device.

BACKGROUND INFORMATION

Current procedures for forming a track in a patient involve first piercing the flank of the patient and, for example, the kidney with a small needle for initial access. Proper imaging verifies the correct placement. The track is then opened to a desired size by any of a variety of methods.

In a first method, a balloon catheter, back loaded with a sheath, is inflated to an appropriate pressure. This pressure provides the radial force to dilate the track. After the track is dilated, a sheath is passed over the balloon to maintain the track opening. For different track sizes, an array of balloons of varying sizes are needed because the maximum dilation force is obtained only when the balloon is fully inflated. For each different size balloon catheter, a different sized sheath must be used. This method of dilation, however, as opposed to the second method of renal dilators and sheaths, provides equal radial force around the circumference of the balloon and along its length (so called "continuous dilation"). It is generally preferred for this reason and because it minimizes trauma to the patient. However, balloons are prone to inflate with irregularities when the resistance of the surrounding tissues is irregular such as encountered with segments of scar tissues. The weakest area of the tissue is dilated faster forming a waist, the remaining tissue is dilated as the inflation pressure is increased, but at a slower rate. This phenomenon is referred to as "waisting."

A second currently used method of dilation involves the use of several passive renal dilator and sheaths. The renal dilator shears tissue as it is introduced into the track. The passive dilator is a plastic tube with a bullet tip; the passive sheath is a hollow tube. Both dilators and sheaths have specific preset diameters. For example, the size of renal dilators range in diameter from 8 F to 30 F in increments of about 2 F (F refers to "French," a unit of measurement of diameter, where 1 F=0.013 inch). An 8 F dilator is first used to dilate the track, followed by substitution of incrementally larger dilators until the desired track size is obtained. Thus, multiple exchanges of dilators are necessary. This method causes undesirable shearing of tissue.

In a third method, an elongate tube made of elastic material such as rubber is mounted and stretched longitudinally onto a rod, thus decreasing the radial size of the tube. The mounted tube is inserted into a track opening and released from the rod, thus increasing the radial size of the tube to its original size. Using this system, one needs a series of tubes having varying radial sizes to fit the desired track opening. Selection of the desired size tube permits the dilation of a track opening in one step. However once a tube is selected and positioned, the size of the track cannot be modified.

In a fourth method, the dilators have a tapered distal end formed by a compacted slit tube or a series of foil wrapped onto one another to form a cone which may be gradually expanded by manual insertion of a rod within the interior of the dilator until the wall of the dilator's distal end have become parallel.

In yet another method, a mesh tube is introduced percutaneously in the body using a needle and stylet. Once placed into the body, the needle and the stylet are removed from the mesh and a passive dilator is inserted manually to expand the radius of the mesh tube. Using this system, still several passive dilators are needed to gradually reached the desired track size.

A major inconvenience of these methods is that for each desired track diameter, one must use a specific dilator or balloon and a specific sheath. The limited availability of sizes for these components limits the availability of track sizes that maybe obtained. Further, once these components are inserted, the track size cannot be constricted.

SUMMARY OF THE INVENTION

To overcome the deficiencies of these methods, the present invention provides dilation systems and related methods in which progressive dilation to a desired track size is accomplished using an actuation device with a dial-a-size functionality integrated into a single device. Further, dilation to a desired track size and maintenance of the track opening are also integrated into a single device. The integrated device provides increased versatility and flexibility to the physician. Further, the dilation systems of the present invention provides for the homogeneous application of radial forces along the length of the dilating element, and homogeneous resistance against countering radial forces applied to the dilating element by the more or less compliant surrounding tissues of the body opening into which the dilating element is inserted. Several dilation systems are presented in the detailed description that follows which combine in a variety of ways various dilating elements and actuation mechanisms. The elements of each of the systems described specifically hereinafter may be combined with one another to achieve other acceptable dilation systems that result in functionally similar devices.

In one aspect of the invention, the dilation systems includes a dilating element and an actuation mechanism, the latter interfaces between the dilating element and the user. The dilating element can be radially expanded to any of a plurality of diameters. The dilation of the dilating element is directed and controlled by the actuation mechanism. Similarly, once dilated, the dilating element may be radially constricted to any of a plurality of diameter using the actuation mechanism.

In one embodiment of the dilation system, the dilating element is a rolled foil. The rolled foil may be used alone or in combination with other dilating elements. The rolled foil develops radial outward forces when compressed to a diameter smaller than its original resting diameter and inward radial forces when dilated larger than its original resting diameter. When used from an initial compressed state the rolled foil is preferably used as a dilating element and also as a sheath once in the dilated state. When used from an initial resting state to a dilated state the foil is preferably used as a sheath in combination with another dilating element of the invention. Other embodiments of the dilating elements suitable for use in combination with the rolled foil are, but not limited to, the following: malecots; jacks; parallelograms; balloons; wire baskets; pivots; telescopic cannulas, chain links; longitudinal springs, meshes and braids. These elements may be used as a single unit or a series of them arranged head-to-tail, within the rolled foil. In one embodiment, two rolled foils may be used as dilating element, one in a compressed state contained within the lumen of the other one, the other one in the resting state.

In another embodiment, the rolled foil includes a series of locking mechanisms that permits the selection and retention of a variety of dilated or compressed diameters.

In one embodiment the locking mechanisms includes two series of interfitting structures, one series is located on a segment of the foil, the other series is located on a second segment of the foil spatially proximal to the first series. The series of intermitting structure may be bumps and notches, protrusions and recesses, tongues and recesses, tongues and holes, and rivets and holes. In another embodiment, the locking mechanism further includes a trigger which interfaces between the two series of interfitting structures to facilitate the locking and releasing of the locking mechanism by engaging or disengaging of the one series of interfitting structure vis-a-vis the other. In one embodiment, the locking mechanism provides the locking of motion unidirectionally to prevent for example either excessive dilation or deflation of the dilating element. In another embodiment, the locking mechanism provides the locking of motion bidirectionally.

Certain embodiments of the dilating element provide dilation along a certain length of a track of a body without forming a waist. Waistless dilating elements include a combination of a hard or noncompliant expandable cover with a variety of dilating elements. Hard or non-compliant expandable covers include, but are not limited to, the following: rolled foils, meshes and braids. Suitable dilating elements include, but are not limited to, any one, or a series of one, of the following: malecots; jacks; chain links; longitudinal springs; parallelograms; balloons; wire baskets; telescopic cannulas, and pivots. A preferred embodiment at least includes a rolled foil. Another preferred embodiment includes a balloon covered by a mesh or braid.

In other preferred embodiments, the dilating element is covered by other expandable sheaths, such as expandable membranes, nonexpandable membranes may also be used as sheath but require to be compacted on the deflated dilating element.

The actuating mechanism includes a dial and a transmission mechanism. The dial and the proximal end of the transmission mechanism are housed in a handle. The handle and the dial includes a series of markings or indices graduated preferably in unit of French or other suitably unit proportional to the diameter of the dilating element. The dial can occupy a variety of configurations in relation to the handle, each configuration identified by a different index and for selection by the user. The dial is connected to the proximal end of the transmission mechanism within the handle. In some embodiments, the dial is connected directly to the transmission mechanism, if no amplification of motion is required. In some other embodiments the dial is indirectly connected to the transmission mechanism, through an amplifying mechanical structure.

Also in some embodiments, the dial is directly actuated by the user and transfer motions from the user to the transmission mechanism. Yet in other embodiments, the dial indirectly transfers motions from the user to the transmission mechanism. For example, the dial includes an electronic interface which include, but is not limited to, a power source, a circuitry, a series of switches, and a motor connected to the transmission mechanism.

In some embodiments, the transmission mechanism transfers a motion of the dial to the dilating element. The motion may either be longitudinal or rotational. In these embodiments, the transmission mechanism includes at least one tubular member such as, but not limited to, cannulas, rods, shafts, or needles.

In some other embodiments the transmission mechanism converts and transfers motions from the dial to the dilating element. In these embodiments the transmission mechanism includes at least a tubular member and at least one thread. In some other embodiments the tubular member includes two threads. In certain embodiments one thread is located at the proximal end of the tubular member for engagement with the dial, the other at the distal end for engagement with the dilating element. In other embodiments, the two threads are located in the distal end, one for engagement with the proximal end of the dilating element, the other for engagement with the distal end of the dilating element.

In another aspect, the invention is directed to methods for dilating a track of a body. In one embodiment the method includes the following steps: insertion in the track of a dilating element capable of expanding to any of a plurality of diameters; expansion of the dilating element to any of a plurality of diameters. The expansion of the dilating element is controlled by the user which actuates the actuation mechanism. In other embodiments, the methods also include the step of introducing a sheath over the dilating element in a dilated state to maintain the track dilated to the diameter selected from the plurality of diameters. Yet other embodiments of the methods include the step of removing the dilating element from the track.

Alternatively, the dilating element may be removed after having been deflated to any of a plurality of diameter inferior to the diameter of the dilated state.

In certain embodiments of the methods according to this invention, the dilating element is first inserted into the track of a body and then dilated. Yet in other embodiments, the dilating element is first dilated, then inserted into the track of a body in the dilated state.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIG. 1D shows a cross-sectional representation of the dilation system of FIGS. 1A–1C dilating a nephrostomy track.

FIGS. 4A–4F show cross-sectional schematic representation of separate embodiments of locking mechanisms with partial views only for FIGS. 4E and 4F.

FIG. 9B show a distal portion and FIG. 9C shows a proximal portion.

FIGS. 9D–9I show in various schematic views of the embodiment of FIG. 9A: a perspective view in FIG. 9D; a top view in FIG. 9F; a side view in FIG. 9G; a longitudinal sectional view in FIG. 9H; a side view in FIG. 9I, and a distal portion of a perspective view in FIG. 9E.

FIG. 10A shows a portion of a longitudinal sectional view of one embodiment of a dilating element and transmission mechanism according to the invention.

FIG. 10B shows a cross sectional view of the transmission mechanism of FIG. 10A.

FIG. 11 shows a portion of a longitudinal sectional view of one embodiment of dilating element and transmission mechanism according to the invention.

FIG. 14A with one unit of a dilating element; FIG. 14B with five units of the same dilating element disposed in a series; FIG. 14C with two units of the same dilating element disposed in a series.

FIG. 18A; relaxed state of the dilating element; FIG. 18B, compressed state of the dilating element; FIG. 18C transmission mechanism and dilating element.

FIG. 22 shows a side view of one embodiment of a dilation system with a portion of transmission mechanism according to the invention.

FIG. 23A shows a side view of one embodiment of a dilation system with a portion of transmission mechanism according to the invention.

FIG. 23B shows a perspective view of the dilating element of FIG. 23A.

FIG. 24A shows a perspective view of a embodiment of a component of a dilating element according to the invention.

FIG. 24B shows a side view of a series of components of FIG. 24A forming a dilating element in a relaxed configuration with a portion of the transmission mechanism.

FIG. 24C shows a perspective view of the dilating element of FIG. 24B in a dilated, compressed state.

FIG. 24D shows a front view of the dilating element of FIG. 24C.

FIGS. 33A–33B shows two views of an embodiment of the dilation system of the invention with a longitudinal section in FIG. 33A; and a cross section of the distal end in FIG. 33B.

FIGS. 34A–34B shows two longitudinal sectional views of an embodiment of the dilation system of the invention: in the deflated state in FIG. 34A, and in the dilated state in FIG. 34B.

DESCRIPTION

Figure 1A:
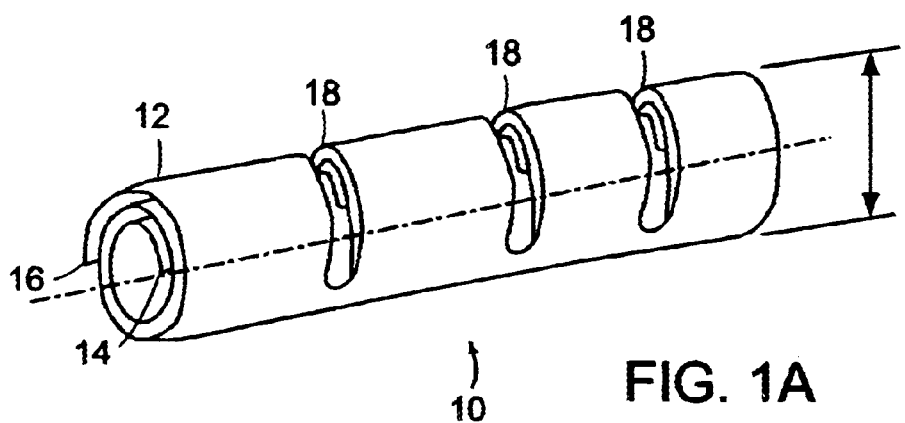
FIGS. 1A–1C show perspective schematic representations of a dilation system of the invention: dilating element alone, FIG. 1A; dilating element in combination with the activation mechanism, FIG. 1B; dilating element in combination with the actuation mechanism and handle, FIG. 1C.
Figure 1B:
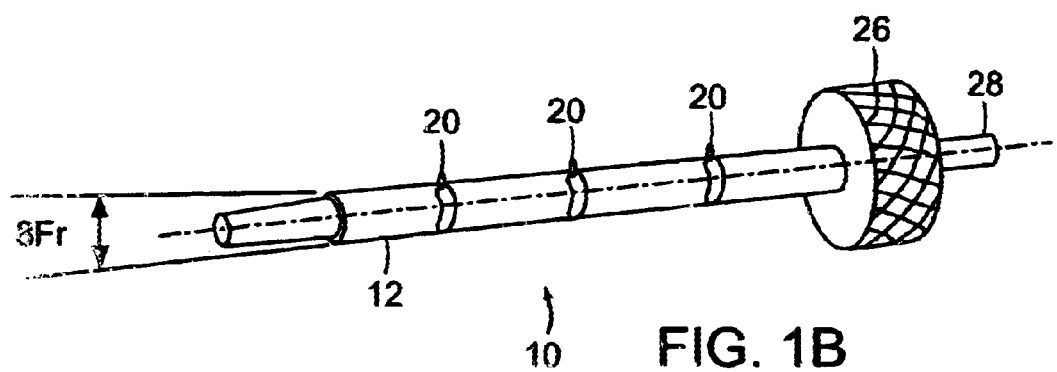

To achieve the objects and in accordance with the purpose of the invention, as embodied and broadly described herein, the inventive dilation systems and methods integrate dilation and user actuation in a single device. More specifically, the dilation systems and methods combine a dilating element to open a track in a patient and an actuation mechanism to interface with the dilating element and the user. These combined elements in a single dilation system provide progressive radial expansion (dilation) and/or force dilation that dilates a track opening to any desired size (from, for example, any of 8 F to 30 F) with minimum trauma or tear to the tissue. These dilation systems eliminate the exchange of multiple separate dilators.

The progressive radial expansion of the dilating element may be performed continuously or by small discrete increments. Also, dilation may be interrupted and resumed to reach various dilation sizes in stages as desired or required by the procedure without exchanging or withdrawal of the device from the track. In some cases, the apparatus of the present invention permits to reduce the size of the dilating element after reaching the desired targeted dilated state or once the procedure is completed. This permits to minimize trauma to the tissue. Also, it facilitates the removal of the dilating element, in particular when the dilating element is also used as a sheath or prosthesis.

Dilating elements of the present invention come in two categories: 1) active dilating elements; 2) passive dilating elements. An active dilating element is an element that tends to spontaneously dilates with no additional forces and/or the dilation of which is controlled directly by the actuation device, e.g., balloons, tubular radial spring, malecots. Active dilating elements may be used alone in a single dilation systems or may be used in combination with a passive dilating element to provide greater versatility or improved functional characteristics. A passive dilating element is an element that can reach and maintain a dilated state but requires the use of an active dilating element to reach its dilated state, e.g., passive rolled foil, braided mesh or covering membrane. In certain embodiments, the dilating element may additionally act as prosthesis to maintain the opening of the track to the desired size. In preferred embodiments, the passive dilating element is used as both sheath for the active dilating element and prosthesis. In some of these embodiments the dilating element may also include multiple locking/release mechanisms to maintain the diameter of the dilating element to the desired track size, or release it to its initial reduced size to facilitate its removal from the track.

All of the dilating elements described herein may be used in combination with an outer protective cover. The cover may be rigid, such as a mesh or braid, or flexible such as a silicon or latex membrane, or a combination of both. Some of the embodiments represented in the accompanying figures of the dilating elements described below show such a membrane or a protective oversheath while some others do not. It is to be understood that all of these dilating elements may be used with such a membrane or protective oversheath.

The integrated actuation mechanism includes a dial-a-size structure, and transmission mechanism for actuation of the dilating element. Both of these structures are connected and housed in a handle for direct activation by the user.

The dial-a-size structure is an element that can adopt a variety of positions or configurations within the handle such as a rotating wheel, a sliding rod, or a series of push buttons, for example. The dial-a-size structure is movably supported within a groove or recess of the handle. The movements of the dial-a-size structure are graduated by indices, markings, or reference marks thereon and on the handle. The separation between the indices markings, or reference marks is directly proportional to a desired dilation size and are preferably graduated in diameter units or French units. The positions of the dial-a-size are selected by the user. The dial-a-size structure is also directly connected to the transmission mechanism, or it may be connected indirectly if amplification of motion is desired.

Alternatively, the dial indirectly transfer motions on switches or buttons from the user to the transmission mechanism. The dial may include an electronic interface. For example, the electronic interface can include, but is not limited to, a power source, a circuitry, a series of switches, and a motor, electricly connected within the circuitry. The motor is connected to the transmission mechanism.

The transmission mechanism is a mechanical structure or a combination of several mechanical structures which transfers the motion applied on the dial-a-size structure to the dilating element and optionally converts it. For example, the transmission mechanism can be a rod, a shaft or a hollow tube or a plurality thereof which transfers a longitudinal sliding motion of the dial-a-size to a sliding motion of the distal end of the dilating element. In this type of actuation mechanisms the dilating element is preferably an element which expands radially when compressed longitudinally. Such dilating elements includes, but are not limited to, balloons, malecots, rubber tubes, mesh and braids. Alternatively, the transmission mechanism 1) converts first the motion applied to the dial-a-size, then transfers the converted motion to the dilating element, 2) transfers first the motion applied to the dial-a-size to the dilating element and then converts it before applying the converted motion to the dilating element, or 3) converts first the motion applied to the dial-a-size then transfers it to the dilating elements, and then converts it again before applying to the dilating element.

For example, the dial-a-size is a rotating wheel and the dilating element expands upon longitudinal compression. The transmission mechanism converts the rotating motion into a longitudinal motion. Such transmission mechanism can be an axial rod, shaft or hollow tube connected proximally to the dial-a-size and distally to the dilating element. Either one of the proximal or distal connecting point is fixedly connected, the other one is movably connected by a thread or screw structure such that upon rotation of the rod, the movably connected point move longitudinally. In some embodiments, the thread is located at the proximal end of the rod and movably interacts with a corresponding complementary thread in the dial-a-size structure, and the distal end is fixedly connected to the dilating element by a washer. In other embodiments, the thread is located at the distal end of the rod and movably interacts with a corresponding complementary thread located or affixed to the dilating element, and the proximal end is fixedly connected to the wheel of the dial-a-size.

Optionally the rod may include a second thread to convert the rotating motion in a longitudinal motion opposite to the first longitudinal motion to apply a greater and faster compression rate to the dilating element and thus faster dilation. In this case, both threads wind on the rod in opposite directions, clockwise and counterclockwise, such that upon rotation of the rod opposite longitudinal motions are applied to the dilating element. If the opposite longitudinal motions are converging the dilating element is compressed and thus expands. If the longitudinal motions are diverging, the dilating element is released, and thus deflates or relapses to a smaller radius.

In some cases, the transmission mechanism is composed of a pair of rods which move concertedly either in a same direction or in opposite directions. Alternatively, one rod remains fixed while the other moves bidirectionally. In some cases, the pair of rods is located axially. In other cases, each rod is located at an opposite equidistant position from the axis of the dilating element and is connected to the dial-a-size and the dilating element by a pivotal bar if opposite directions of movement are desired, or by a fixed bar if concerted motion is desired. Such transmission mechanism may be used in combination with dilating elements such as malecots and parallelograms, for example.

In yet other embodiments, the transmission mechanism is a valve which control the flow of a fluid entering a balloon chamber.

These and other types of mechanical structures which convert one type of motion, e.g., lateral, rotational, longitudinal, etc., into another, with or without amplification or inversion of motion, are well known in the art and can be sized and adapted for use in the actuation components of the instant dilation systems.

In summary, the present invention provides a single device for controlled radial expansion of a track of a patient, for example a nephrostomy track. The invention also integrates a dilator and a sheath in one device. After initial entry with an 8 F needle portion of the device, an expansion member provides high dilation forces controlled by a dial-a-size actuation system connected to dilation systems and the handle. The device also provides over the wire type functionality, i.e., permit passage of a guide wire. The benefits of the above-described devices also include true radial dilation by the expansion member and the lessening of tissue trauma around the track area. The single step procedure eliminates the conventional exchange of dilator sheaths while achieving track sizes from 8–30 F through the use of a single device.

The inventive dilation systems, including the particular embodiments shown and described herein, may be adapted for use in endoscopic procedures. Instead of using a rigid element that connects the dilating/expansion element to the dial and handle, a flexible coil or wire can be used, making this invention and the various embodiments described herein applicable to endoscopic applications in the gastrointestinal and urologic lumens of the body for dilating strictures and obstructions inside the body, for example.

The above dilation systems also can be utilized in the placement of PEGS, for opening constrictions in the vascular system or during intervention in other organs and lumens of mammals. These described uses of the inventive dilation systems are preferable and exemplary and are by no means limiting. It is to be understood that other uses are contemplated and within the scope of this invention.

These and other actuation mechanisms are further described and illustrated in specific embodiments disclosed below.

To form a track of desired size in a patient, the skin of the patient is punctured with a needle for initial access. A guide wire is then inserted in the track through the needle. Then, the dilating element is inserted in a compressed state into the track over the guide wire. Alternatively, the needles and the dilating element are inserted together. The needle then is contained within the dilating element and only the sharp distal tapered tip of the needle protrudes from the distal end of the dilating element.

Once the dilating element is inserted into the track of a patient, actuation of the dial by the user will initiate radial expansion of the dilating element, thus dilating the track of the patient. Motion of the dial by a certain amount, will actuate the transmission mechanism and the dilating element of a proportional amount. Thus dilation of the track is directly proportional to the amount of motion applied to the dial. Thus by marking and graduating the various positions of the dial-a-size in the handle, a user may select the desired amount of expansion applied to the dilating element, and thus the desired dilation.

Once the track is dilated to the desired size, a prosthesis or sheath may be inserted into the track to maintain the track opening, and the dilating element is removed. Alternatively, the dilating element may be both a dilating element and a prosthesis, in this case, there is no need for this second step, and then the actuation mechanism is disconnected from the dilating/prosthesis element.

Reference will now be made in detail to the present preferred embodiments of the invention, examples of which are illustrated in the accompanying drawings.

Tubular Radial Spring with Active Foil Torsional Element

In a first embodiment shown in FIGS. 1A–1D, a dilation system 100 and related method according to the present invention includes an instrument 100 (showing in FIG. 1C) having an active dilating element 10 which can act as both a dilating element and a prosthesis. The dilating element 10 is a rolled or coiled foil which operates like a tubular radial spring 12. The spring 12 develops radial forces which are either directed outward if the spring is compressed, or directed inward if the spring is expanded radially from its relaxed state. The spring 12 will thus preferably be used as an active dilating element in a compressed state, and as a passive dilating sheath in an expanded state. The spring 12 is formed by rolling one edge 14 of an elastic quadrangular plate over the plate toward the opposite edge 16 of the plate such that it forms a tube the cross section of which forms a spiral. The plate is preferably of a foil type, either metallic or plastic, and is relatively very thin so that it can be spirally rolled, or coiled, into a tube. The spring 12 (FIGS. 1A and 1C), in its wound or compressed state (FIG. 1B), is small in diameter, for example, about 8 F. When released, the spring 12 tends to unwind. The torsional strength of the spring 12 should be greater than the resistance offered by the tissue track so that the spring 12 dilates the tissue upon release. The controlled release of the spring 12 can be calibrated to provide a progressive continuous dilation force, i.e., the same dilation force for each increments of release.

Figure 1C:
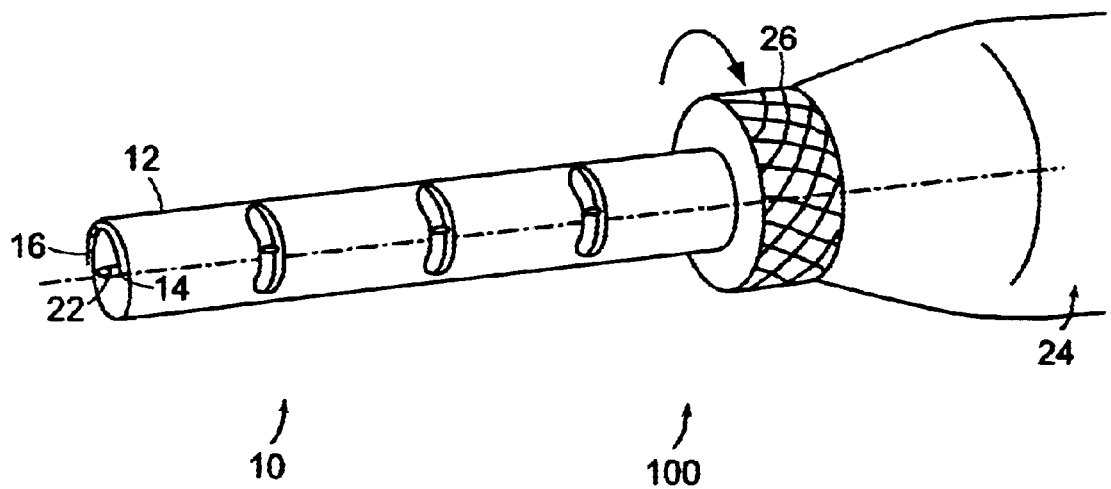
Figure 3A:
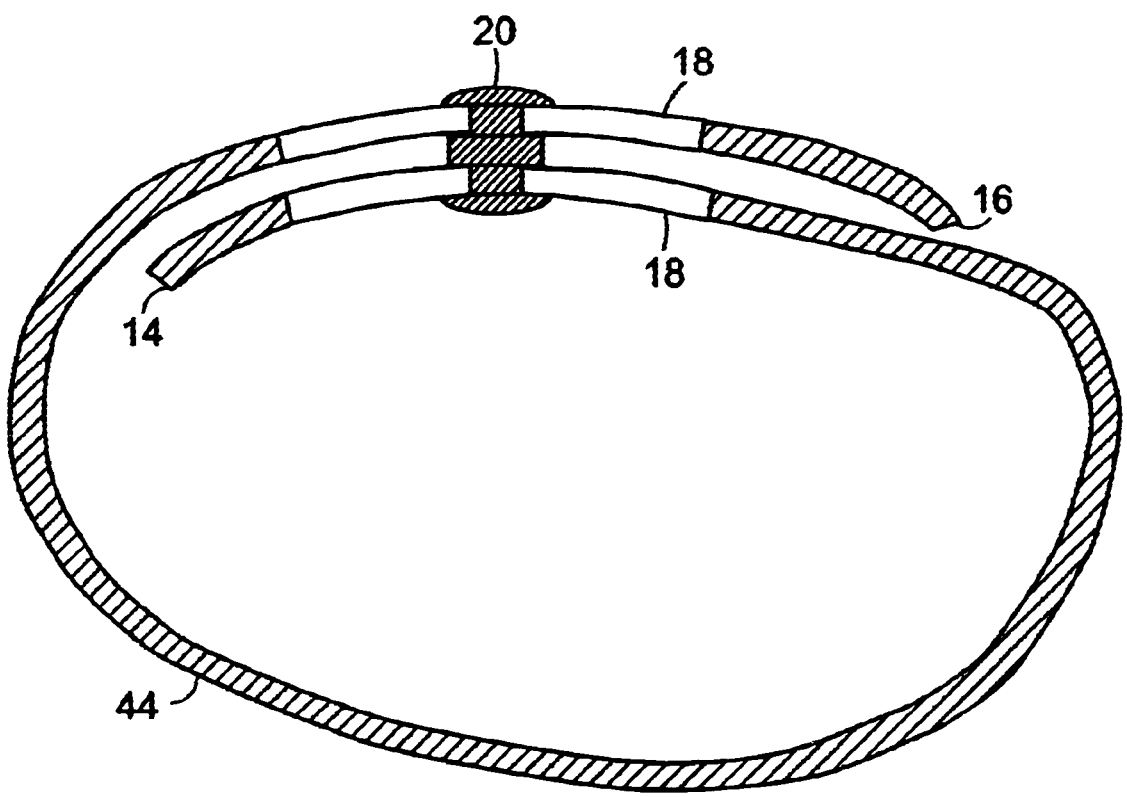
FIGS. 3A–3B show cross-sectional schematic representation of separate embodiments of locking mechanisms for use in dilation systems of the invention, with a partial view only for FIG. 3B.
Figure 3B:
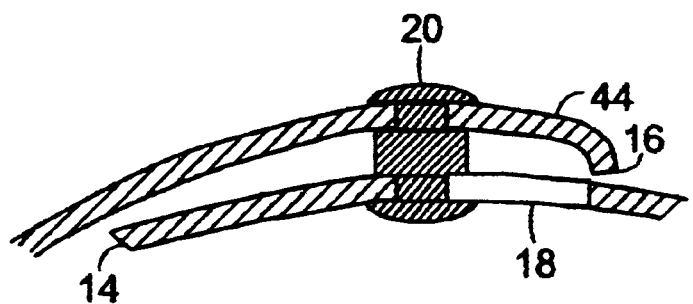

As shown in FIG. 1A, the spring 12 includes a locking mechanism. A series of circumferential slots 18 are cut in the spring 12 along its longitudinal axis to retain small rivet-type structures 20 (FIGS. 1B–1C) that move inside the slots 18. The rivets 20 are mechanically linked to an actuating rod 22 contained within the spring 12 and connected to the dial 26 in the handle 24 for user actuation. The actuating rod 22 is connected to a dial 26 with locking mechanism. As shown in FIG. 1C, upon rotation of the dial 26, the rivets 20 move in the slots 18, permitting the release and enlargement of the spring 12 within the track of the patient. FIGS. 3A and 3B show other embodiments of the rivets and slots locking mechanism which may be used with a passive foil as described herein after. FIG. 1D shows the enlarged spring 12 acting as a prosthesis to maintain the dilator size of the track opening to access the kidney percutaneously.

Figure 2:
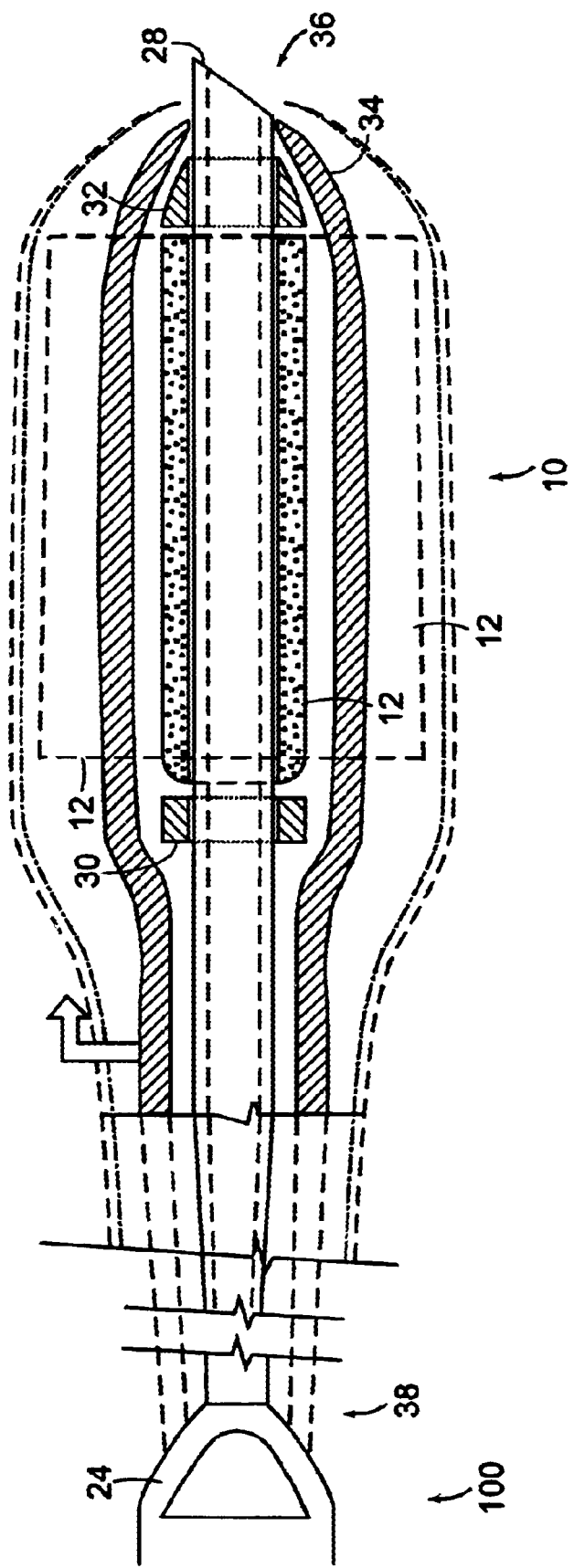
FIG. 2 shows a longitudinal sectional schematic representation of an embodiment of the dilation system of the invention, in the compressed state (solid lines), and dilated state (broken lines).

FIG. 2 shows a modified dilation system 100 using the active foil of the first embodiment. In FIG. 2, the spring 12 is tightly wound and mounted around a needle 28 and restrained from longitudinal movement by a washer 30 and a tip 32. A braid or mesh 34 surrounds the spring 12 and needle 28 and is fixed to the needle 28 at the distal end 32. At its proximal end 38, the braid is connected to a "dial-a-size" actuation mechanism 40 and handle 24. When the actuation mechanism 40 pulls the braid tightly, radial expansion of the spring 12 is restrained. As the braid is loosened, the braid moves distally (as represented by the thick arrow pointing to the left in FIG. 2) and expands radially due to the torsional force supplied by the spring 12. The spring 12 expands radially and the track of the patient is thereby opened. The loosened position of the braid 34 is shown by the outer thick dashed lines in FIG. 2. The radially expanded position of the spring 12 is also shown by dashed lines between the tip 32 and the washer 30. Thus actuation is achieved by pulling or releasing the braid 34. No slots 18 or rivets 20 as shown in FIGS. 1A–1D are needed in the dilation system of FIG. 2.

It is also contemplated for the dilation system of FIG. 2 to act as a prosthesis or sheath to maintain the track opening after dilation. In this case, the braid 34 would be detachable from the distal end 36 of the needle by, for example, pulling the braid with sufficient force. The tip 32 to the left of the spring 12 in FIG. 2 would not be incorporated in this device so that the needle 28 could be pulled out, leaving only the spring 12 to act as a prosthesis. In this case, it may be necessary to incorporate a locking mechanism such as slots 18 and rivets 20 of FIGS. 1A–1D or any other locking mechanisms disclosed herein after and illustrated in FIGS. 3A–B, 4A–F, 5, and 6A–E into the device to restrain further radial expansion of the spring 12 once the desired track opening is reached.

The dilation system of this first embodiment, and shown and described in connection with FIGS. 1A–1 and 2, has the following advantages:

a. True radial (continuous) dilation is obtained due to the circumferential structure of the spring 12.

b. Differing sized tracks of desired diameters can be obtained due to the controlled release and actuation provided by the integrated handle.

c. The "waisting" phenomenon that occurs during the use of balloon catheters is avoided. In the present embodiment, the torsional strength of the spring 12 is sufficiently stronger than the resistance offered by the tissue, and the consistent tubular profile exerts the same force on the tissue circumferentially and along the entire length of the spring 12. The spring 12, therefore, evenly opens the tissue.

d. Since the spring 12 opens outwardly, an annular space is created permitting passage of a guide wire 42 (not shown). In addition, as shown in FIG. 2, the spring 12 can be mounted onto an initial entry needle 28 and introduced into the patient.

e. Due to the hollow annular space created upon enlargement of the spring 12, this dilation system may serve as a prosthesis to maintain the track opening and eliminates the need for a separate sheath. Hence, this dilation system integrates a dilator and a sheath.

f. The removable handle includes a mechanism to comfortably allow the calibrated and controlled release and enlargement of the spring 12, providing the "dial-a-size" functionality.

The spring 12 also can be used most optimally to act as both a dilator and a sheath, or, in the alternative, used only as a universal sheath (in a prosthesis role) in conjunction with balloon or plastic dilators as described below.

The spring 12 shown in FIGS. 1A–1D and 2 can be utilized for other percutaneous access procedures to dilate and open the exterior skin of a patient to obtain access inside the body. Although the above discussion involved maintaining a track size of 8 F to 30 F, the same foil structure can be used for laproscopic and general surgery to dilate, open, and act as a prosthesis for access inside the body.

Passive Foil Torsional Element: Universal Sheath

In this embodiment, the dilation system 100 comprises both an active and a passive dilating element. The passive dilating element is a sheet of metal, for example, or any other material that presents adequate properties, that is-rolled into a tube such that the wall of the tube in cross section forms a spiral, with segments of its wall overlapping each other. In this embodiment, the spiral tube (hereinafter "universal sheath") does not possess substantial torsional strength to dilate spontaneously surrounding tissue and is thus preferably used in combination with the conventional plastic dilators or balloon catheters or with any active dilating elements described herein. Alternatively, the universal sheath possesses a torsional strength only in the dilated state to permit the easy release of the dilated state to a smaller original state to facilitate removal of the sheath from the track of the patient. The sheath is manufactured by rolling a sheet of metal or other material having appropriate flexible characteristics, around a cylinder to cover approximately 0.75–10 times the periphery of the cylinder. Preferably, the sheet winds 1.25–2 times the periphery of the cylinder. In the case of plastic dilators, an initial entry needle 28 initiates the track and an array of plastic dilators are exchanged to enlarge the track. The universal sheath 44 acts as a prosthesis to keep the track open. Although several dilators may be used, only one universal sheath is needed to act as the prosthesis. Various sizes of the sheath can be achieved via controlled dilation and/or release using in combination with the actuation mechanism any of a variety of locking mechanisms as illustrated in FIGS. 3A–B, 4A–F, 5, and 6A–E. The locking mechanisms may be manufactured on the sheet prior to coiling it by a variety of processes either integrated in the manufacturing of the sheet such as extrusion or cold draw, or in a separate step after manufacture of the sheet, such as stamping, machining, laser cutting photo etching, for example.

FIG. 3A shows a cross-sectional view of the universal sheath 44 with a rivet 20 and slots 18 as locking mechanism. Both overlapping inner segments 46 and outer segment 48 of the universal sheath 44 comprise a series of spatially overlapping slots 18. The radius of the universal sheath 44 is controlled by the rivet 20 which provides sufficient resistive friction forces to impede opposite radial movements of the inner segment 46 and outer segment 48. Upon, the application of progressive radial forces provided by a dilating element such as a balloon catheter or other dilating devices as described herein, sufficient to overcome the resistive friction forces of the rivet 20, the inner segment 46 and outer segment 48 slide outwardly in opposite directions, expanding progressively and continuously the radius of the universal sheath 44 and dilating the track opening of the patient. FIG. 3B shows a cross sectional view of an alternate embodiment of the universal sheath 44 with rivets 20 and slots 18 as locking mechanism. In this embodiment, only a series of slots 18 is located on the inner segment 48 of the universal sheath 44. The outer segment having a series of holes 50 not wider than necessary to hold the rivets 20 therethrough. An alternate embodiment (not shown) would present the series of slots 18 on the outer segment 48 and the series of holes 50 on the inner segment 46. Expansion of the universal sheath 44 is activated as described for FIG. 3A with the sliding of only one segment, the segment having the slots 18.

Figure 4A:
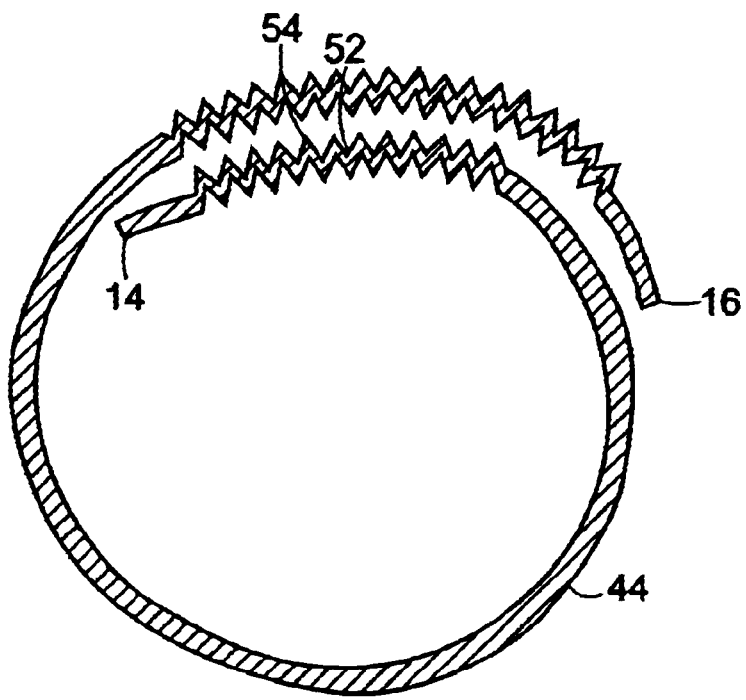
Figure 4B:
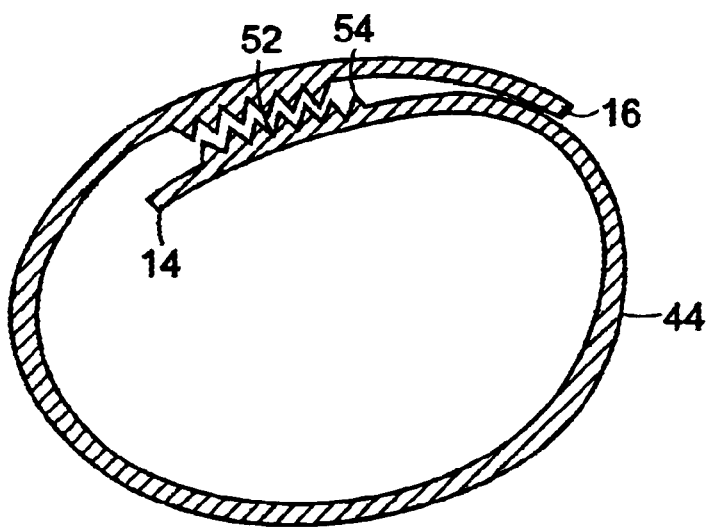

FIGS. 4A–F show various embodiments of another type of locking mechanism for use in the passive universal sheath using a plurality of interfacing recesses 52 and bumps 54. The recesses 52 and bumps 54 may be present on either one of both of the inner and outer surfaces 56 and 58, respectively of either one of both inner and outer segments 46 48, respectively. In FIG. 4A, the recesses 52 and bumps 54 are present on both surfaces 56 and 58 of both segments 46 and 48 such that clamping would occur regardless of which segment is the inner or outer segment. In FIG. 4B, the recesses 52 and bumps 54 are present on only one surface of each segment, i.e., the inner surface 56 of the outer segment 48 and the outer surface 58 of the inner segment 46. In this embodiment, clamping occur only when the inner surface 56 of the outer segment 48 is positioned on top of the outer surface 58 of the inner segment 46. Such embodiment would permit the easy release of the universal sheath 44 from the track of the patient once no longer needed by dilating the sheath so both edges 14 and 16 slide by each other and the position of the inner and outer segments is reversed such that the inner segment 46 becomes an outer segment 48', and the outer segment 48 becomes an inner segment 46'. In this reverse configuration no clamping occurs and the sheath can be contracted by an activating mechanism and released from the track with minimal shearing to the tissue. To avoid excessive dilation of the track prior to releasing the sheath, it is preferable to imprint or positioned the recesses 52 and bumps 54 the closest as possible of the edges 14 and 16 of the foil. To obtain a good grip or clamping between the surfaces 56 and 58 and to facilitate the reversion of the segment's position, the foil is preferably manufactured so as to form a "G" as shown in FIG. 4C with the recesses 52 and bumps 54 or tongues 60 pointed away from each other, where the original folding of the foil is in a reverse configuration. The segment's positions are then reversed as shown in FIG. 4D to bring the surfaces bearing the recesses 52 and bumps 54 or tongues 60 in overlapping configuration such that clamping occurs.

FIGS. 4E and 4F show alternative forms of recesses 52 and bumps 54 which may be used to provide clamping or locking of the sheath 44.

Figure 5:
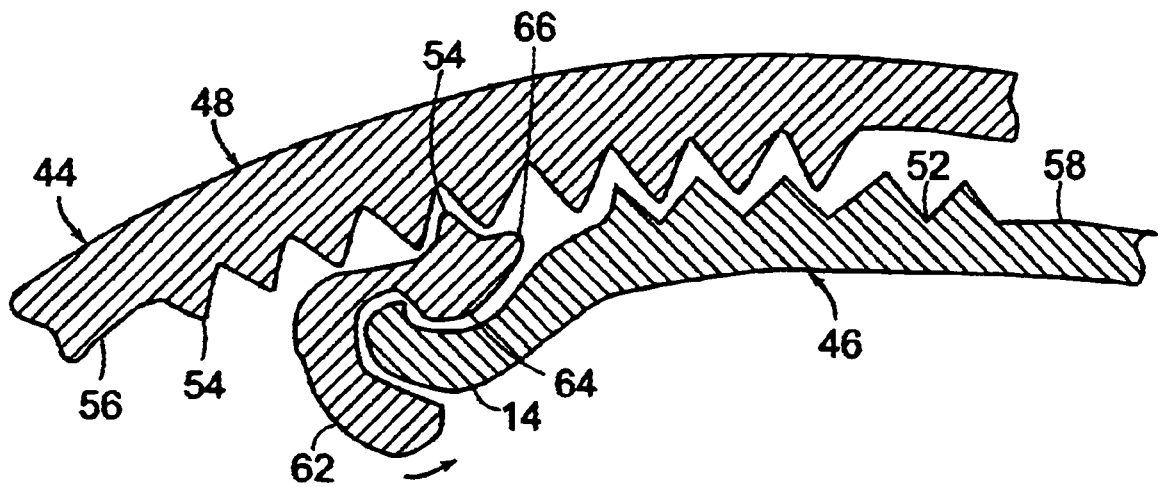
FIG. 5 shows a partial cross-sectional schematic representation of one embodiment of locking and releasing mechanisms for use in a dilation system of the invention.

FIG. 5 shows a portion of a cross sectional view of an embodiment for releasing the dilated state of the universal sheath to a compressed or resting state with a lower diameter. In this case the universal sheath 44 is further fitted on the inner edge 14 of the foil with a trigger 62. The trigger 62 is an elongated rod having a groove 64 which wraps around the edge 14 of the inner segment 46. At one of the edge of the groove 64, the trigger 62 also has at least two bumps 54 and 66 which fit into the recesses 52 and bumps 54 of the inner surface 56 of the outer segment 48. When bump 54 is engaged in a recess 52 the trigger is in a resting position, and operates as a lock such that no sliding of the inner and outer segments occurs (as shown on FIG. 5). When the trigger is pivoted as shown by the arrow, bump 66 is now engaged in one of the recesses 52 with the trigger now lifting the edge 14 away from the inner surface 56 of the outer segment 48, and disengaging the bumps of the inner segments 46 from the recesses 52 outer segment either directions of both segments is thus facilitated permitting the dilation or contraction of the sheath. The trigger 62 is connected to the handle 24 (not shown) and can be activated by the user either directly or indirectly.

Figure 6A:
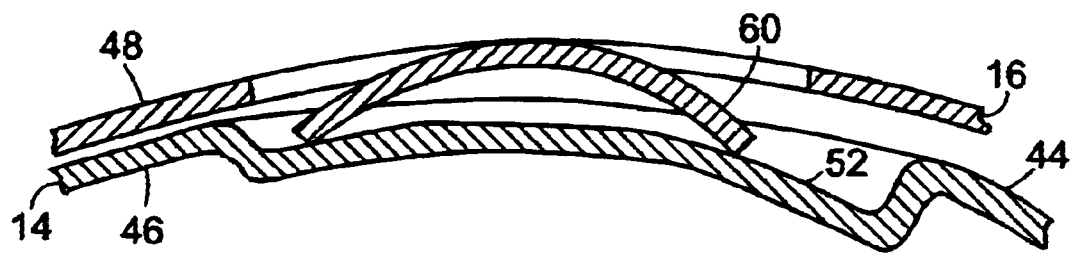
FIG. 6A shows a partial cross-sectional schematic representation of an embodiment of a bidirectional locking mechanism for use in dilation system of the invention.

FIG. 6A shows a cross sectional view of another embodiment of the locking mechanism for use with the universal expandable sheath. In this embodiment, the outer segment 48 includes a series of tongues 60 partially cut out from the foil and bend toward the inner segment 46 to fit within spatially overlapping recesses 52. In this embodiment the movement of the edges 14 and 16 is bidirectionally restrained. Alternatively the position of the recesses 52 and the tongues 60 may be reversed with the tongues 60 being located on the inner segment 46 and having an inverse curvature with regard to the foil or even no curvature at all, and the recesses 52 being located on the outer segment 48.

Figure 6B:
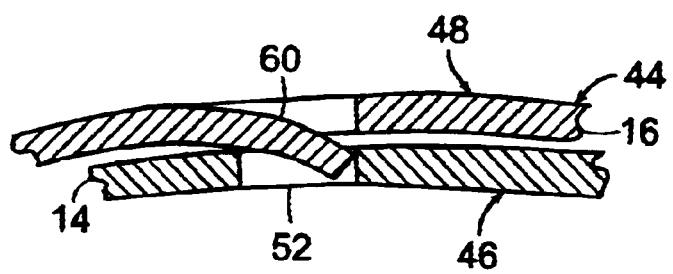
FIG. 6B shows a partial cross-sectional schematic view of an embodiment of a unidirectional locking mechanism for use in dilation systems of the invention.

FIG. 6B shows an alternate embodiment of the locking mechanism of FIG. 6A for unidirectional restraint of movement of the edges 14 and 16 of the sheath 44 to provide locking of either dilation or contraction of the sheath.

Figure 6C:
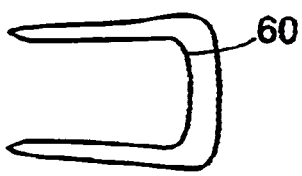
FIGS. 6C–6D show respectively a top view of the upper segment and bottom view of the lower segment of the embodiment of FIG. 6A.
Figure 6D:
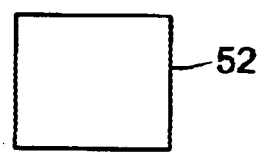
Figure 6E:
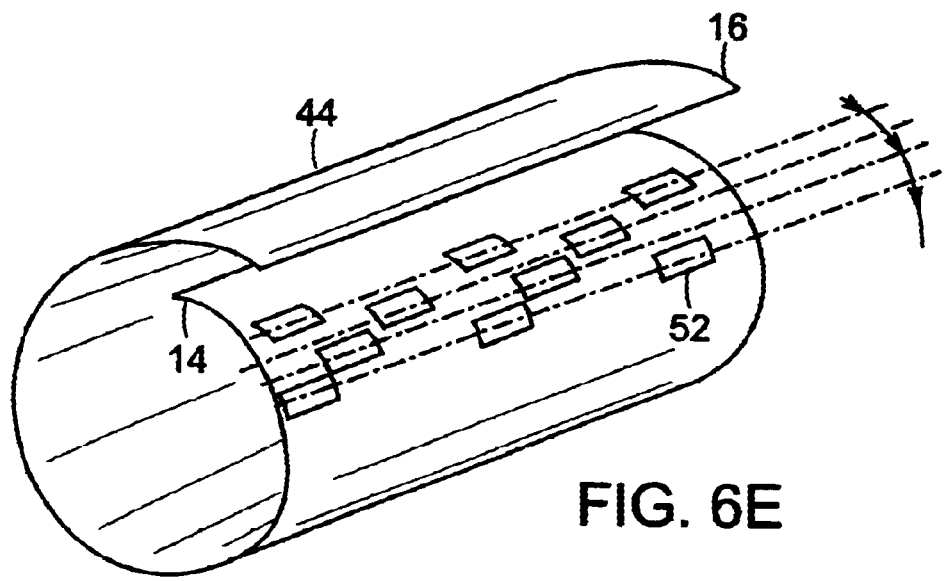
FIG. 6E shows a perspective schematic view of the dilating element featuring the locking mechanism of FIG. 6A.
Figures 7A, 7B:
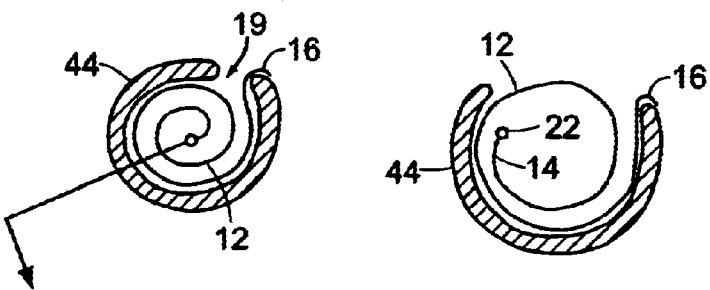
FIGS. 7A–7B show cross-sectional views of an embodiment of a dilating element according to the invention.
Figure 7C:
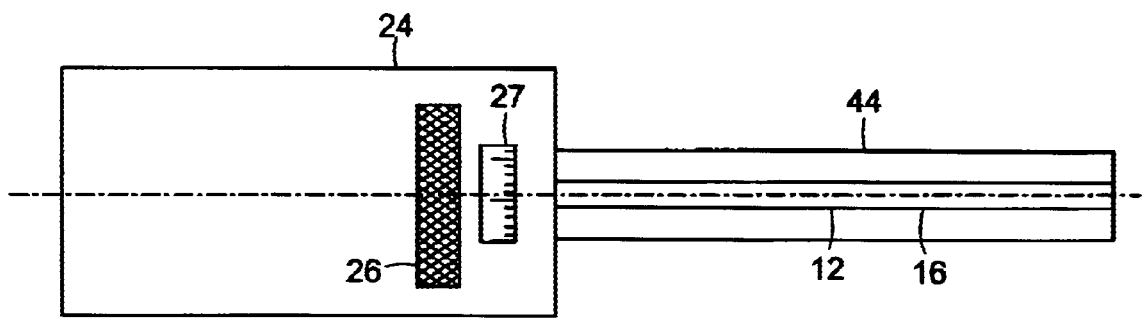
FIGS. 7C–7D show the top and side views of an embodiment of a dilation system having dilating element of FIGS. 7A–7B.
Figure 7D:
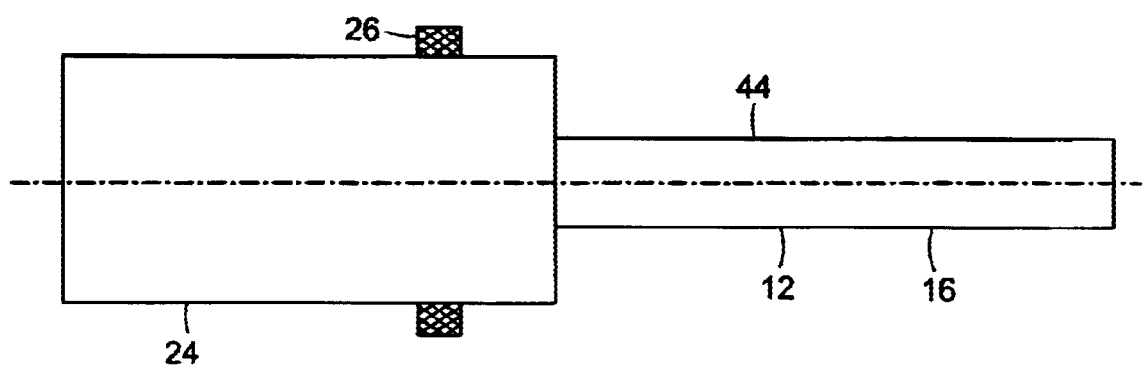
Figure 7E:
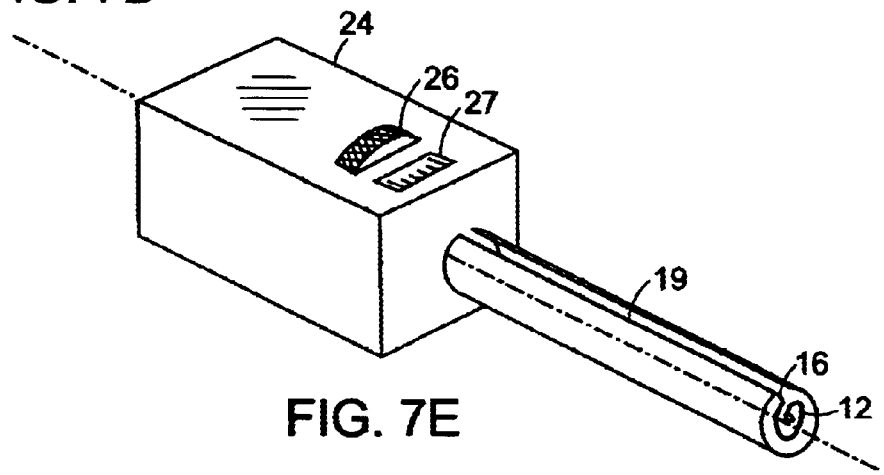
FIG. 7E shows a perspective view of the embodiment of the dilation system of FIGS. 7C–7D.

FIG. 6C shows a top view of a tongue 60 and FIG. 6D shows a top view of a recess 52 of FIG. 6B. FIG. 6E shows a prospective view of the sheath having a series of recesses 52 disposed along the length and separated by discrete increments to provide discrete dilation of the sheath by increment of a portion of French unit.

In another embodiment of the universal sheath, the sheath is formed by winding less than 1 time around a cylinder or is made of a cannula or needle having a longitudinal slot 19 as shown in FIGS. 7A–7E. Enclosed within the sheath 44 is a torsional spring 12. The spring 12 is connected along its length by its outer edge 16 to an edge of the longitudinal slot 19 of sheath 44. The spring 12 is connected at its proximal end 38 to an actuation mechanism that includes a control button or dial 26 and indices 27 graduated in French (F) units. Rotation of the dial 26 applies a torque to the torsional spring 12 to expand the sheath 44 from its initial position shown in FIG. 7A to its expanded position shown in FIG. 7B. Through the use of the control button and indices, the sheath 44 can be expanded to a desired diameter of a track of a patient.

Figure 8A:
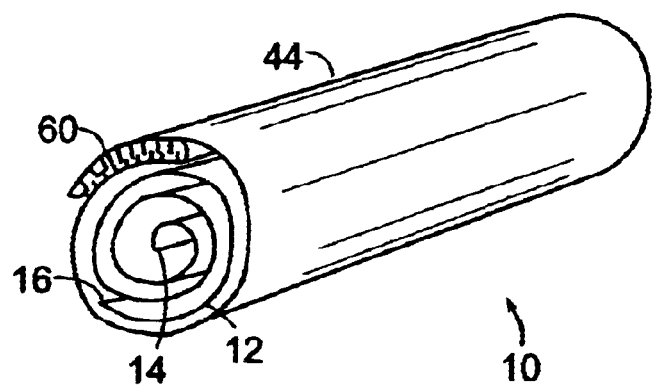
FIGS. 8A–8I show schematic views of various dilating elements having a passive dilating element combined with various active dilating elements according to the invention, with a perspective view for FIG. 8A and longitudinal sectional views for FIGS. 8B–8I.
Figure 8B:
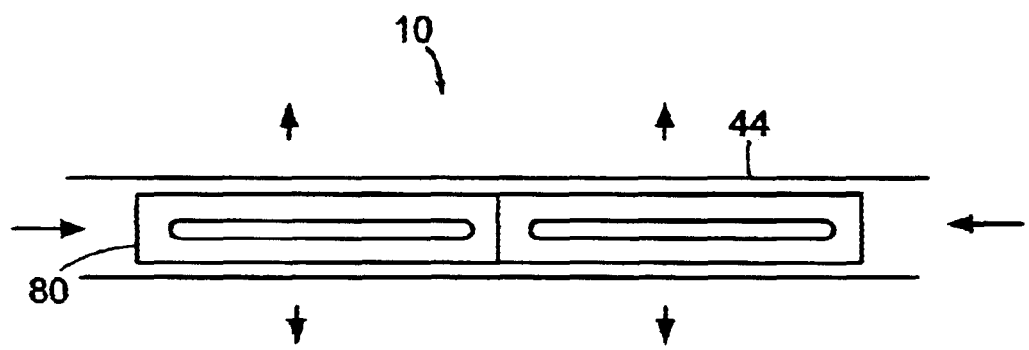
Figure 8C:
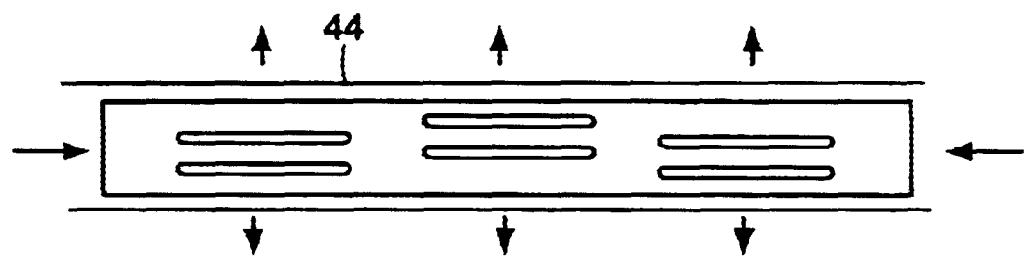
Figure 8D:
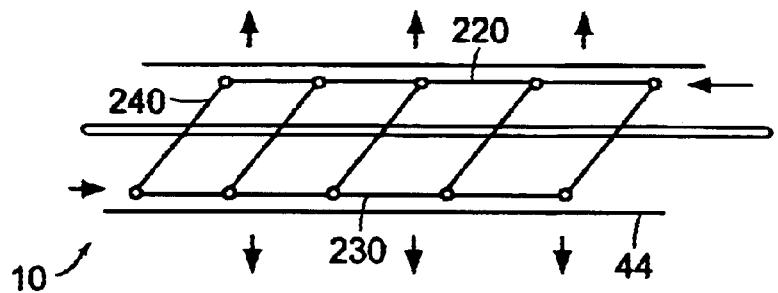
Figure 8E:
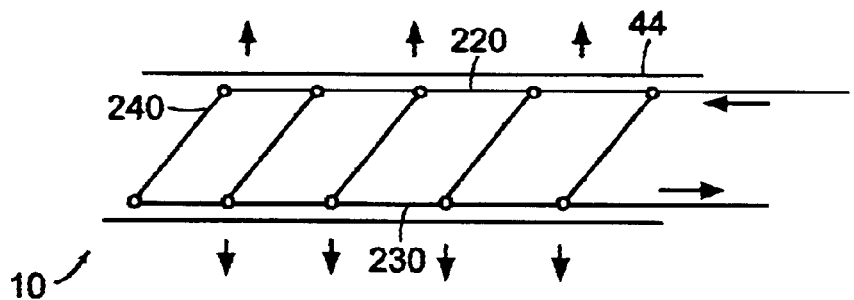

The universal sheath 44 as described above may be used with a variety of known dilating elements, such as passive dilators or balloons catheters. For example, the universal sheath 44 can act as an initial overtube through which all plastic passive dilators are passed. The universal sheath 44 acts as a buffer to minimize the tear to the tissue associated with the introduction of the bullet tipped plastic dilators. Also, the universal sheath 44 may be used with any of the dilating elements as disclosed further herein. For example, FIGS. 8A–8I shows various dilating elements which may be used in accordance with the present invention to provide a progressive continuous dilation controlled by the user through an activation mechanism and a dial-a-size. FIG. 8A shows another embodiment of the universal sheath 44 in combination with the spring 12 described above. FIGS. 8B–8I show various embodiments of dilating elements which convert a longitudinal force or movement into a lateral one or radial one. If the dilating element is a planar element, the longitudinal movement is converted into a lateral movement and the universal sheath then convert the lateral movement into a radial one. If the dilating element is cylindrical or occupies a cylindrical volume, the longitudinal movement is converted directly into a radial one. Appropriate embodiments include, but are not limited to, malecots or slotted tubes shown in FIGS. 8B and 8C, parallelograms shown in FIGS. 8D and 8E, jacks or articulated systems shown in FIGS. 8F and 8G, rubber sheaths or rubber supports shown in FIGS. 8H and 8I. Detailed description of some of these embodiments is provided herein below and in the following sections. In these embodiments, the compression of the dilating element by the application of axial forces in opposite directions at the distal and proximal ends 36 and 38, respectively, of the dilating element creates radial or lateral forces.

Figure 8F:
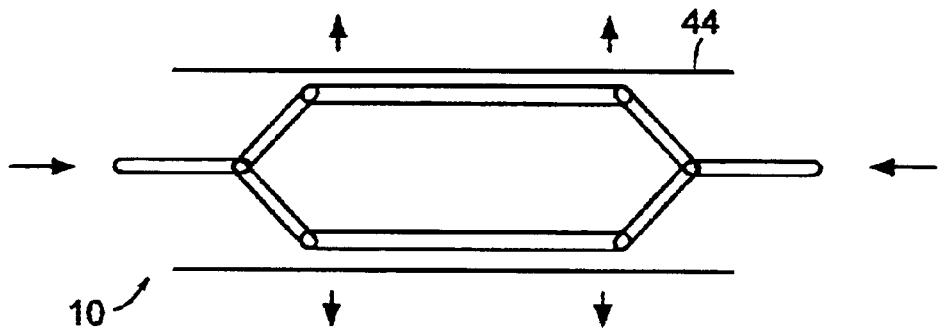
Figure 8G:
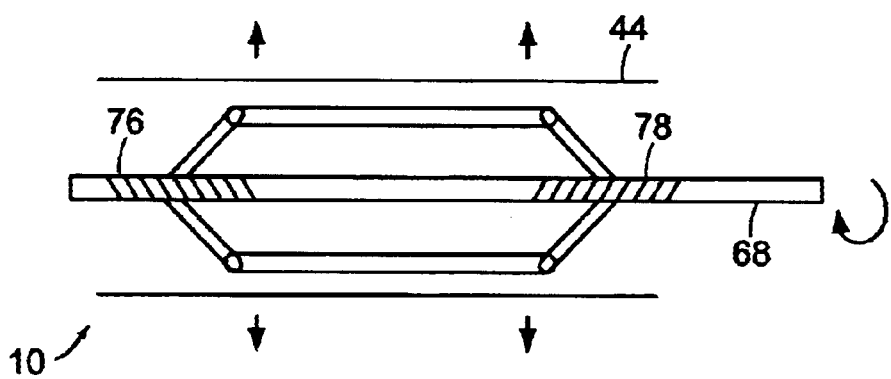
Figure 8H:
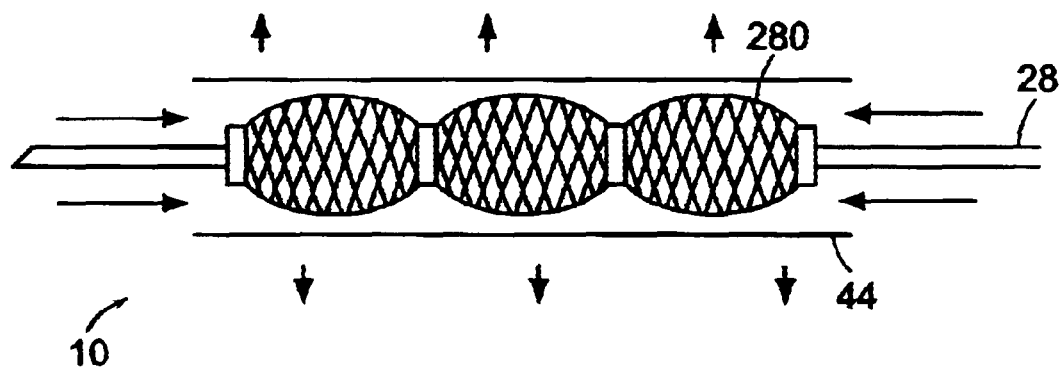
Figure 8I:
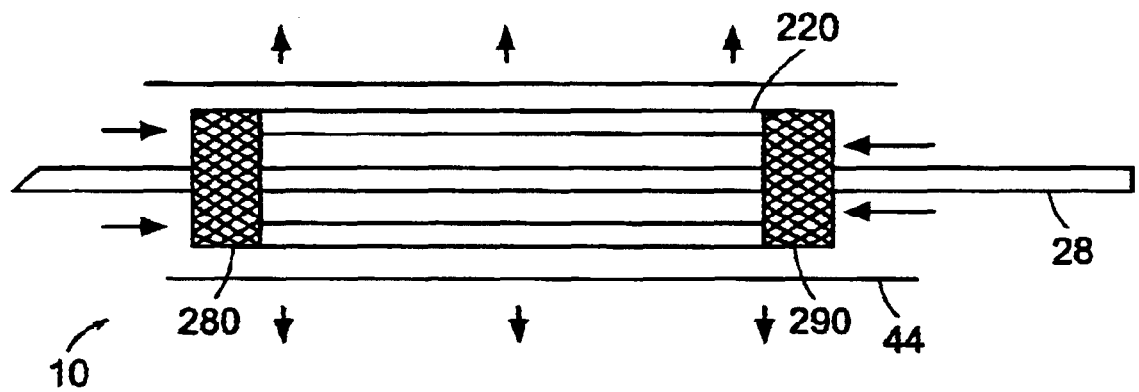
Figure 9A:
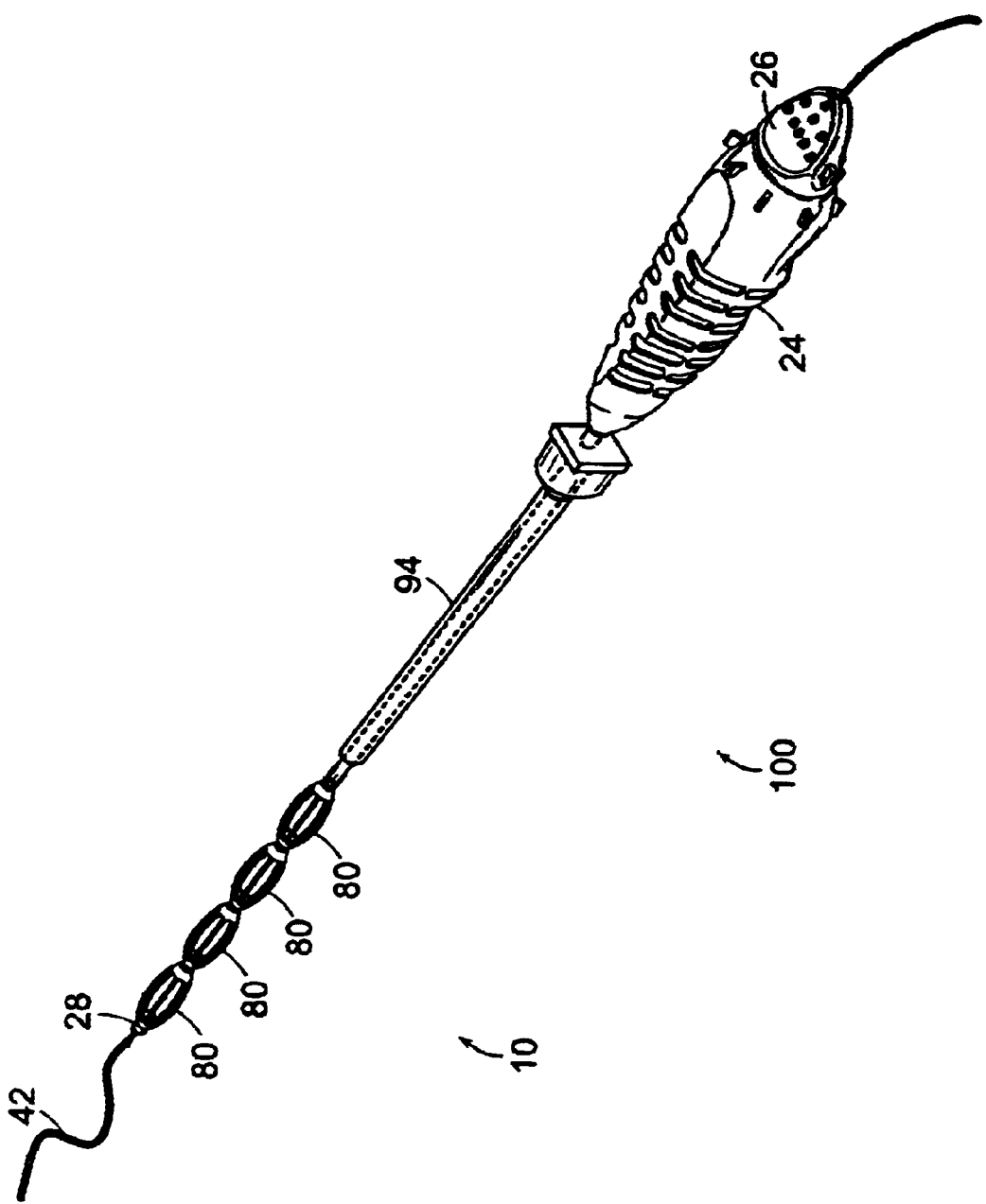
FIG. 9A shows a perspective view of one embodiment of the dilation systems according to the invention.
Figure 9B:
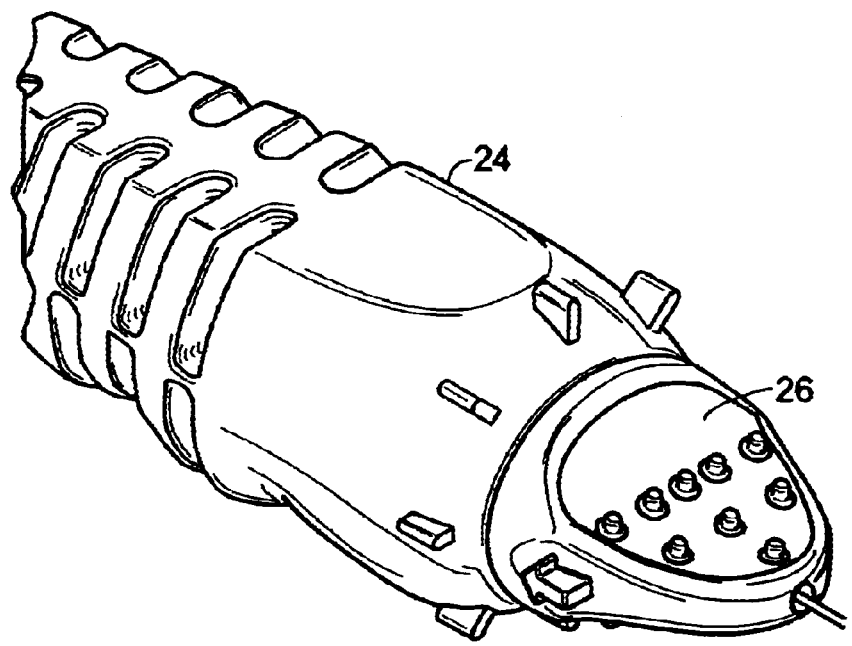
FIGS. 9B–9C show portions of the perspective view of FIG. 9A.
Figure 9C:
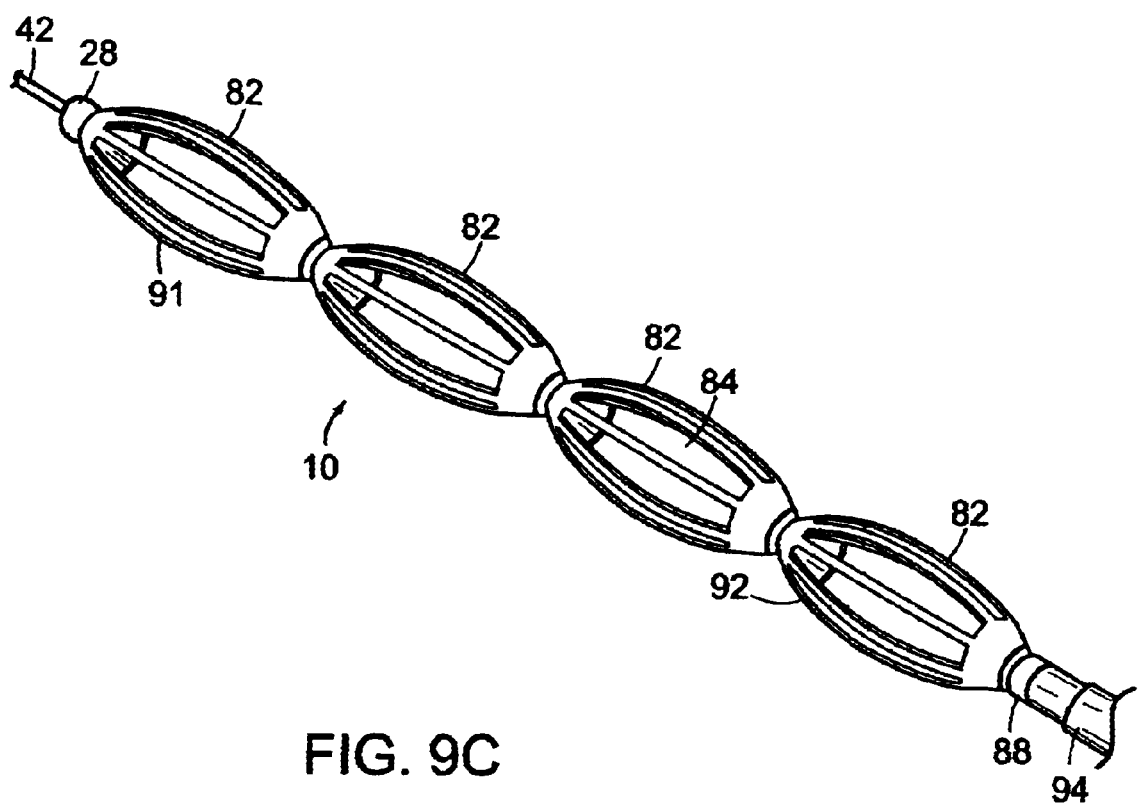

Activating mechanisms to create compression of a dilating element can be a central rod 68 connected to the dilating element axially through a lumen by either threads 70 or washers 72 see FIGS. 8G–8I or by articulated joints 74 as shown in FIG. 8F. The rod 68 may include two threaded segments 76 and 78, a proximal thread 76 for the proximal end 38 of the dilating element and a distal thread 78 for the distal end 36 of the dilating element. Both threads 76 and 78 are directed in opposite directions, for example, the proximal thread directed clockwise and the distal thread 78 directed anti-clockwise, so that rotation of the rod 68 would impart opposite motions of the proximal and distal ends of the dilating element. Alternatively the rod may include only one thread at either one of the proximal or distal end of the dilating element. The remaining end would be maintained stationary by a washer 72 secured to the rod 68. The rod 68 is connected to the dial-a-size 26 in the handle 24.

Other Active Dilating Elements

In addition to certain embodiments of the present invention described above, certain active dilating elements are provided that also provide progressive radial dilation along the length of the track for use with the actuation mechanism in a single device. As in the previous embodiments above, these eliminate the use of various size balloons or the exchanges of the renal plastic dilators. Each of these dilating elements comprises any of a variety of mechanical structures mounted onto an initial entry needle or passed over the initial entry needle. Depending on the type of dilating element, different actuation mechanisms as described earlier may be needed and designed into the handle.

Malecots:

FIGS. 9A–9I. show a dilation system 100 having a series of malecots 80 as dilating element 10 mounted onto a needle 28 and guide wire 42. A malecot is a tube having radial arms 82 formed between slots 84 in the tube as dilating element. The malecot may be made of metal, rubber, or other suitably flexible material. It is contemplated that Nitinol (a nickel titanium alloy) would be a suitable material for a malecot or any of the other mechanical dilating elements described further herein.

When the malecot 80 is axially compressed, the arms 82 deflect radially outward to expand the malecot radially. This radial expansion provides the dilation force. A meshed braid, a sheath or other suitable covering 86 may be placed over a series of malecots sequentially stacked to provide a regular surface for dilation along the length of the dilating element 10.

The actuation mechanism includes a rod or hollow cannula having a screw mechanism with external threads that engage internal threads of the dial-a-size, for example (not shown). The hollow cannula 88 containing the needle 28 is connected to the dial 26. The distal end 90 of the cannula 88 abuts the most proximal malecot 92.

To form a track of a desired size in the patient, the needle 28 punctures the skin for initial access. A guide wire 42 is inserted into the initial track. The dilating element 10 (series of malecots) is inserted into the track over the guide wire 42. Rotation of the dial 26 then advances the cannula 88 distally to compress the malecots 80. Rotation of the dial 26 by a predetermined degree advances the cannula a specific distance to compress the malecots proportionally. Compression of the malecots forces a radial expansion of the malecots, dilating the track of the patient of a certain amount which is directly proportional to the applied rotation on the dial 26. Thus dilation of the track is directly and effectively controlled by the user with the dial-a-size element. Once the track is opened to a desired size, the prosthesis 94 is inserted into the track to maintain the track opening. For example, the prosthesis 94 may be of a size so that it may be slipped between the expanded malecots 80 and the track. The dilating element is then removed.

Alternatively, the malecots may be dilated in their natural state and radially compressed when their extremities are stretched this type of malecots is also referred to as wire basket. The most distal malecot 91 is fixed to the initial entry needle 28. A cannula 88 is attached to the most proximal malecot 92. When the series of malecots is first introduced into the track, the cannula 88 is pulled proximally so that the malecots are in a generally elongated state. Axial displacement of the cannula 88 in the distal direction permits the malecots to expand radially and thereby expand the track of the patient. The amount of expansion is controlled by a dial-a-size 26 which is connected to the cannula 88.

Wire baskets which may be used as dilating elements in the device of the present invention have been disclosed in the U.S. Pat. Nos. 4,590,938 and 5,496,330 for example as well as in U.S. patent application Ser. Nos. 08/656,010, 08/968,906, 09/064,704, 09/064,997, and 09/084,135, the disclosures of which are incorporated in their entirety herein by reference.

Transmission Mechanisms for Malecots

Figure 10C:
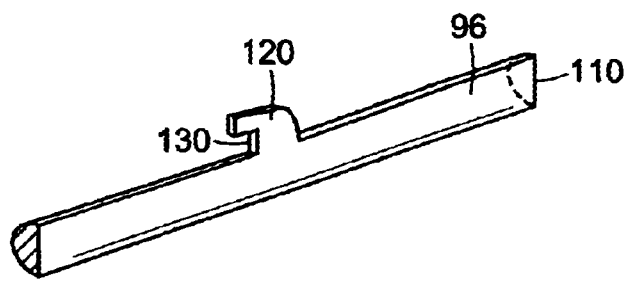
FIG. 10C shows a perspective view of a portion of the transmission mechanism of FIG. 10A.

In the dilation system of FIGS. 9A–9I, the malecots 80 are not compressed independently. FIGS. 10A–C, 11–13 show a transmission mechanism in which the malecots are compressed independently to ensure that the radial expansion of each malecot is substantially the same. FIG. 10 shows two D-shaped needles 96 and 98 abutting one another on their flat faces 110. Each D-shaped needle includes a series of protrusions 120 forming grooves 130. Alternatively, the protrusions 120 and grooves 130 spread along the half-circumference of the needle to provide a proportionally radially distributed compression force on the malecots 80. The needles 96 and 98 are attached to a dial-a-size 26 in the handle 24. Relative axial movement between the two needles controlled by the actuation mechanism causes the malecots 80 to compress longitudinally and expand radially widening a track of a patient. In this dilation system, the malecots can be covered by a meshed braid, or a universal sheath 44 as described earlier or by other suitable structures.

Figure 12:
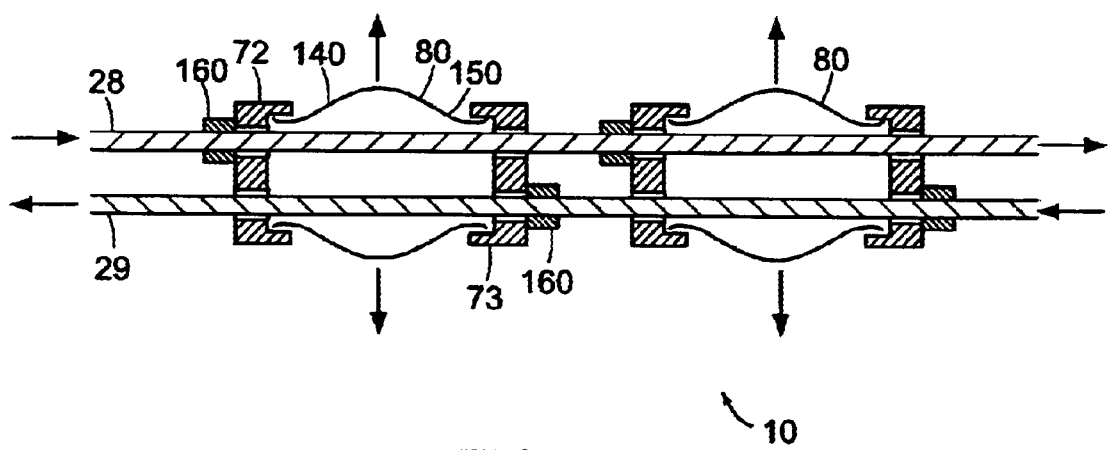
FIG. 12 shows a portion of a longitudinal sectional view of one embodiment of the dilating element and transmission mechanism according to the invention.
Figure 13:
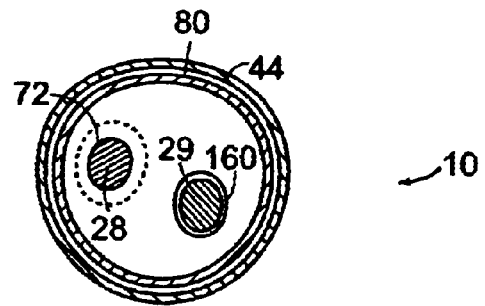
FIG. 13 shows a cross-sectional view of the embodiment of FIG. 12.

FIG. 11 shows a partial view of a transmission mechanism similar to that of FIGS. 10A–C. In FIG. 11, two round needles 28 and 29 are stacked side by side. Each end 140 and 150 of each malecot is retained between or connected to a small flat ring 160. The ring 160 at one end 140 of the malecot 80 is crimped, glued, or otherwise fixedly connected to the first needle 28, and the at other end 150 of the malecot 80 is crimped, glued, or otherwise fixedly connected to the second needle 29. As with the needles 96 and 98 of FIG. 10A, the needles 28 and 29 of FIG. 11 are attached to a dial-a-size 26 in the handle 24. Relative axial movement between the two needles 28 and 29 controlled by the dial 26 causes the malecots 80 to compress and expand radially to open a track of a patient. In this dilation system, the malecots 80 can also be covered by a meshed braid, a universal sheath 44 or by other suitable structures, FIG. 12 (side view) and FIG. 13 (cross-sectional view of FIG. 12) show a transmission mechanism similar to that of FIG. 11. In FIGS. 12 and 13, two round needles 28 and 29 are arranged side by side with separation there between. Each end 140 and 150 of each malecot 80 is retained between or connected to two washer 72 and 73 having holes therein to allow the needles 28 and 29 to pass through. The washer 72 at one end 140 of the malecot 80 is fixed to the first needle 28 via a ring 160 that is crimped, glued, or otherwise fixedly connected to the first needle 28. The washer 73 at other end 150 of the malecot 80 is fixed to the second needle 29 via a ring 160 that is crimped, glued, or otherwise fixedly connected to the second needle 29. The needles 28 and 29 are attached to a dial-a-size 26 in the handle 24. Relative axial movement between the two needles 28 and 29 controlled by the actuation mechanism causes the malecots 80 to compress and expand radially to open a track of a patient. As with the dilation systems of FIGS. 10–11, in this dilation system, the malecots can be covered by a meshed braid, a universal sheath 44 or other suitable mechanical structures, such as those described further herein.

Figure 14A:
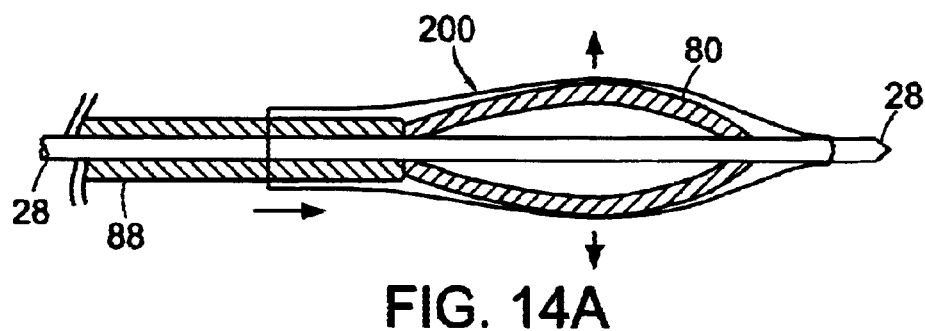
FIGS. 14A–14C show portions of longitudinal sectional views of three related embodiments of the dilation system according with the invention.
Figure 14B:
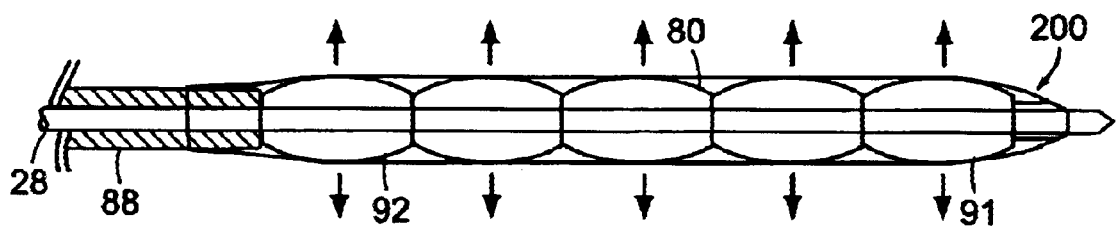
Figure 14C:
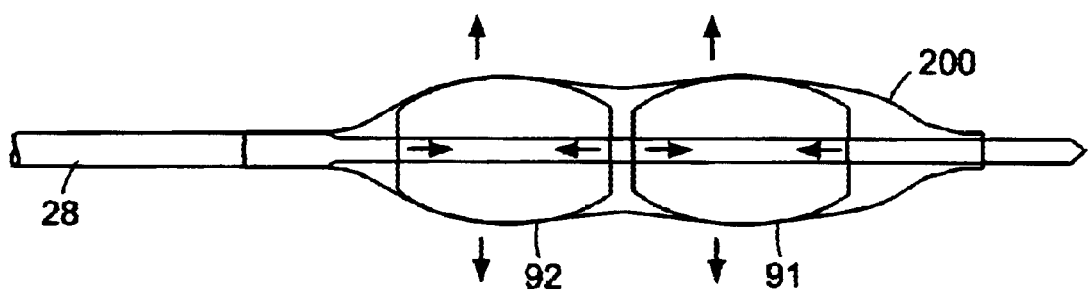

Other Malecot Structures:

The malecots 80 can include any number of shape of slots 84. For example, slots 84 may be shaped to intrinsically limit the radial deflection of the malecots by using a H shape. The malecot shown in FIGS. 14A and 14B may be used alone as shown in FIG. 14A or in a series as shown in FIGS. 14B–C and may use the same actuation mechanism as discussed above and shown in FIGS. 9A–9I, 10A–C, 11 and 12.

Figure 15A:
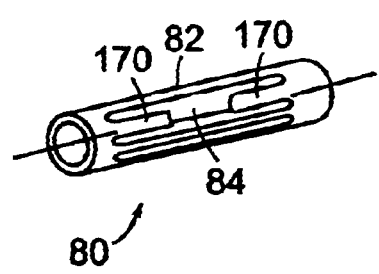
FIG. 15A shows a perspective view of one embodiment of a dilation system according to the invention with a locking mechanism.
Figure 15B:
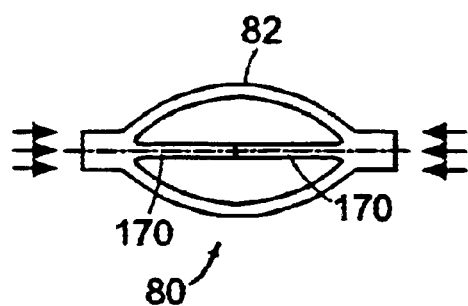
FIG. 15B shows a side view of the embodiment of FIG. 15A.
Figure 16:
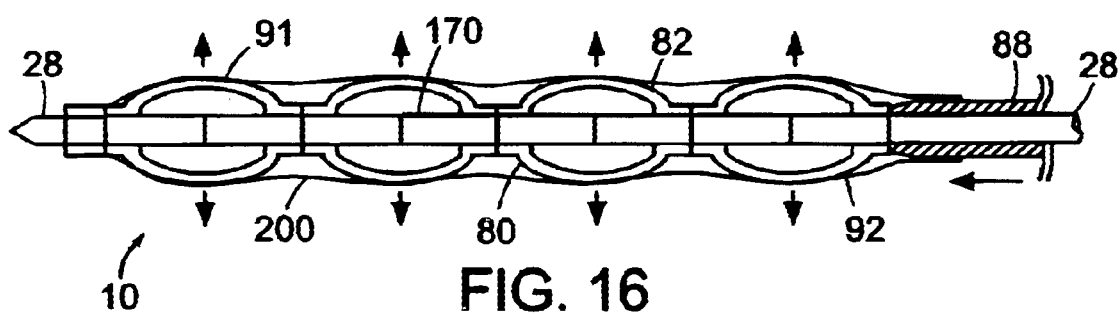
FIG. 16 shows a side view of the distal end of a dilation system having a series of dilating element of FIG. 15B.

The expansion of intrinsically limited-deflection malecots is illustrated in FIGS. 15A and 15B. A dilating element 10 having a series of such malecots is shown in FIG. 16. The malecots 80 include two arms 82, positioned 180 degrees from one another, and two opposing fingers 170 which define H-shaped slots 84. In the uncompressed state, the fingers 170 are not in contact, as shown in FIG. 15A. As the malecot is compressed, the fingers 170 draw closer until they contact each other as shown in FIG. 15B. Upon contact, the fingers 170 do not deflect and thereby limit further radial expansion of the malecot.

Figure 17:
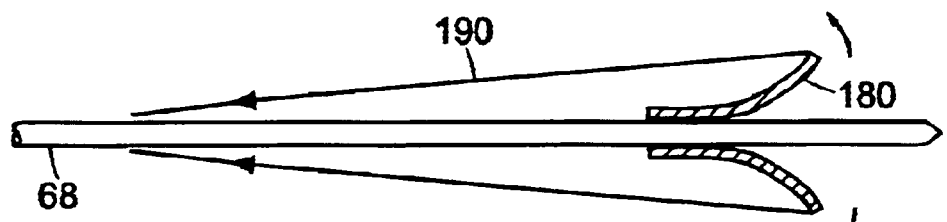
FIG. 17 shows a cross-sectional view of a distal portion of an embodiment of the dilation system according to the invention having a dilating element and portion of the actuation mechanism.

FIG. 17 shows a cross sectional view of a half malecot 180 mounted on a rod 68. Expansion of half-malecot is actuated by pulling wires 190. The half-malecot may be used in a series and use a common or separate actuation system for each half-malecot.

Figure 18A:
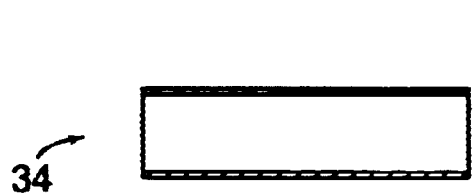
FIGS. 18A–18C shows various portions of a cross-sectional view of the distal end of one embodiment of the dilation system according to the invention.
Figure 18B:
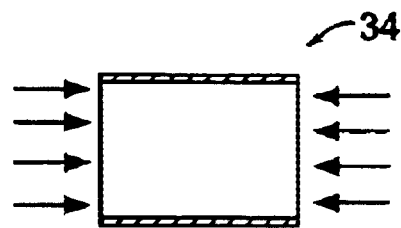
Figure 18C:
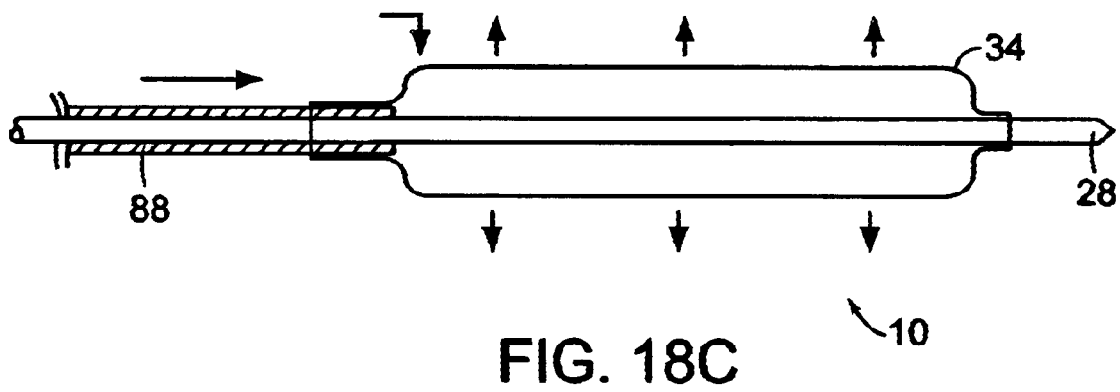

Meshes or Braids:

Mesh or braid may act as dilating element by radially expanding upon axial compression. In FIGS. 18A–18C the mesh 34 may be covered by a membrane 200 that is fixedly connected to a hollow cannula 88 at a proximal end and fixedly connected to the needle 28 at a distal end. The membrane 200 restrains radial expansion of the mesh 34. Axial displacement of the cannula 88 in the distal direction axially compresses the mesh 34 and causes the mesh to radially expand, opening the track of the patient.

Figure 19:
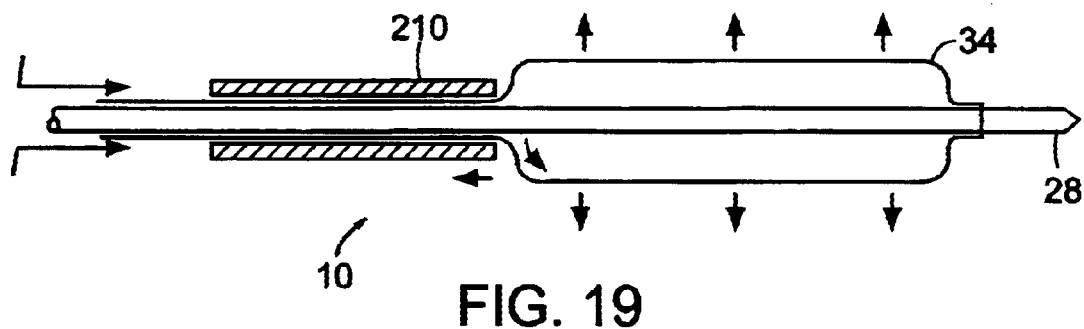
FIG. 19 shows a cross-sectional view of a portion of the dilation system of FIG. 18C with a sheath.

Expansion of the mesh or braid 34 through axial compression may be also controlled by an overtube 210, as shown in FIG. 19. The overtube defines the length of the mesh that will dilate. The tube 210 may be displaced axially in either the proximal or distal direction to limit radial expansion to only certain areas of the mesh and thus control the length of the dilating element.

Figure 20:
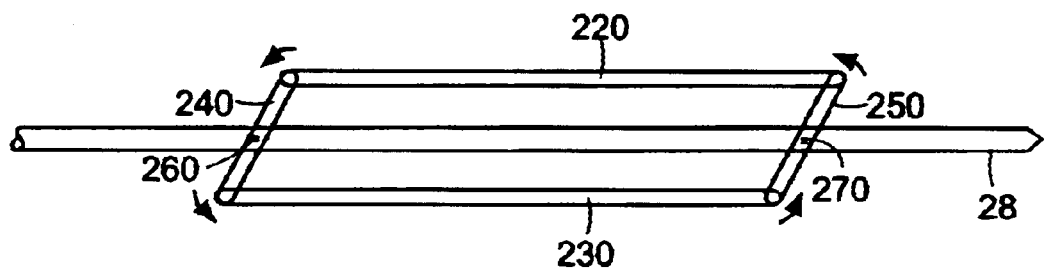
FIG. 20 shows a side view of one embodiment of a dilation system with a portion of transmission mechanism according to the invention.

Parallelograms:

FIG. 20 shows a pair of rigid parallel rods 220 and 230 connected to each other by a pair of rigid links 240 and 250 in a parallelogram arrangement. The links 240 and 250 are pivotally connected to the needle 28 and to the rods 220 and 230. Although not shown in FIG. 16, it is contemplated that this dilation system includes a plurality of such parallelogram arrangements radially spaced around the needle, preferably six or eight rods forming three or four parallelograms, respectively. Actuation of the parallelograms through pull wires, bars, or any other suitable transmission mechanism causes the links 240 and 250 to rotate about pivot points 260 and 270, causing the rods 220 and 230 to displace radially and dilate a track of a patient.

Figure 21:
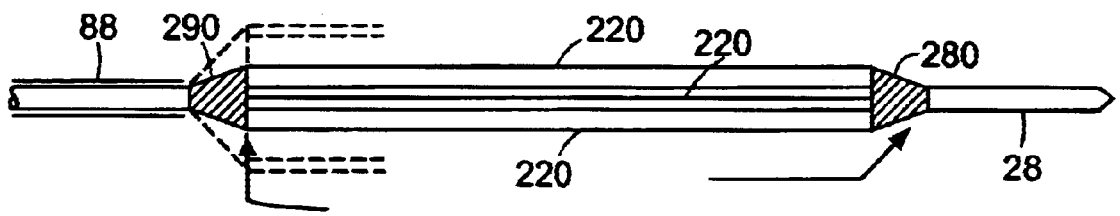
FIG. 21 shows a side view of one embodiment of a dilation system with a portion of transmission mechanism according to the invention.

FIG. 21 shows another parallelogram system having a plurality of rigid parallel rods 220, preferably six, mounted around a needle 28 by distal and proximal rubber supports 280 and 290, respectively. When the rubber supports 280 and 290 are compressed, for example, by a cannula 88 as in FIGS. 9A–9I, the rubber supports radially expand to force the rods 220 to displace radially and dilate a track of a patient. This type of parallelogram operates like a malecot except that the dilation forces are applied regularly with the same intensity along the length of the rods. The rods and links of FIGS. 20 and 21 are made of metal or any other suitable rigid material. Parallelograms may be used in combination with a mesh or braid, universal sheath 44 or any other suitable material.

Jacks:

FIG. 22 shows a dilation system having a jack actuated by a threaded needle. The jack is composed of a series of articulated rods 300 connected between each other by joints 302 and connected to a ring 160 at the proximal end and a nut 310 at the distal end. Preferably the jack has one, two or four joints 302. The ring 160 is movably supported around the needle 28 so rotation of the needle 28 does not impart motion to the ring 160. The ring 160 is spatially immobilized by a cannula 88 (not shown). The proximal end of cannula 88 rests against the handle 24 (not shown) and the distal end of cannula 88 rests against the proximal end of the dilating element. The nut 310 has a thread (not shown) which engages with the thread 320 of the needle 28. Upon rotation of the needle 28, the nut 320 is displaced axially along the needle 28 compressing the articulated rods 300 forcing them to move radially outward, thus dilating the track of a patient. A reverse motion of the needle 28 would release the compression forces on the articulated rods 300 and allow the release of the dilated state.

Alternatively, the jack comprises two nuts 310 having opposite threads to engage two opposite threaded portion 320 on the needle 28. Rotation of the needle 28 imparts a converging or diverging motion of the nuts 310 dilating or releasing the jack.

Preferably the jack comprises a plurality of articulated rods 300 radially distributed around a central axis to provide a regular distribution of the dilating forces along the circumference of the track. Preferably the jacks comprises six to eight articulated rods 300. A dilating element can comprise one jack or a plurality of jacks arranged in a series along the cannula 88. Jacks may be used in combination with the mesh or braid, universal sheath 44, or any other suitable material.

Pivots:

In FIGS. 23A and 23B, a plurality of pivots 330, are pivotally joined to the needle 28 at varying angular orientations around the axis. Actuation of the pivots 330 by a pull wire 190 (not shown), or other suitable actuator, causes the pivots 330 to rotate about their pivot point 340 causing their extremities 242 and 244 to move radially outward. A braid mesh or universal sheath can be placed over the entire structure to obtain continuous and regular dilation. Pivots may be used in combination with a mesh or braid, universal sheath 44 or any suitable material.

Chain Links:

In FIGS. 24A–24D, a series of chain links 350 are pivotally connected to each other head-to-tail, forming a chain, by a pin 380 or rivet or any other suitable connecting element. Each link 350 includes a protrusion 360 at each end and a hole within the protrusion. A pull wire 190 is connected to each link 350 by a hole 390 in the middle of each link (not shown) so that the links are aligned axially when the pull wire 190 is in a relaxed state. When the wire 190 is pulled to a tense state, the links pivot with respect to one another and assume the formation shown in FIGS. 24C and 24D to dilate a track of a patient. Chain links may be used in combination with a mesh or braid, universal sheath 44 or any other suitable material.

Figure 25:
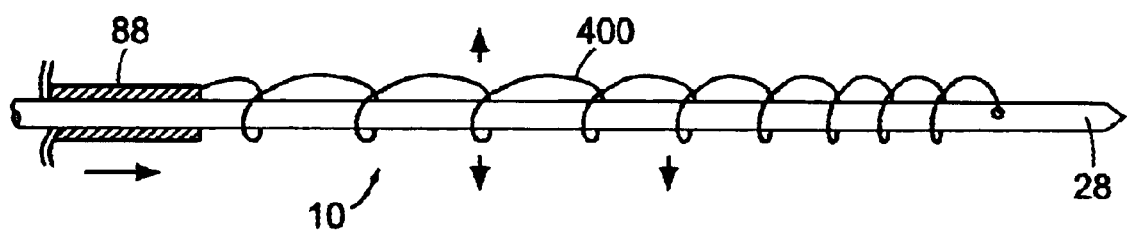
FIG. 25 shows a side view of one embodiment of a dilation system with a portion of transmission mechanism according to the invention.
Figure 26A:
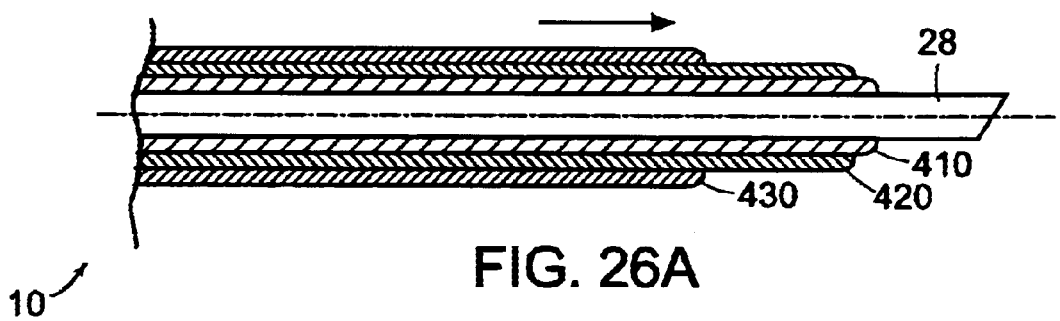
FIG. 26A shows a longitudinal sectional view of the distal end of one embodiment of the dilation system of the invention.
Figure 26B:
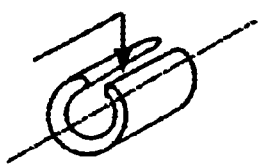
FIG. 26B shows a perspective view of a component of the embodiment of FIG. 26A.
Figure 26C:
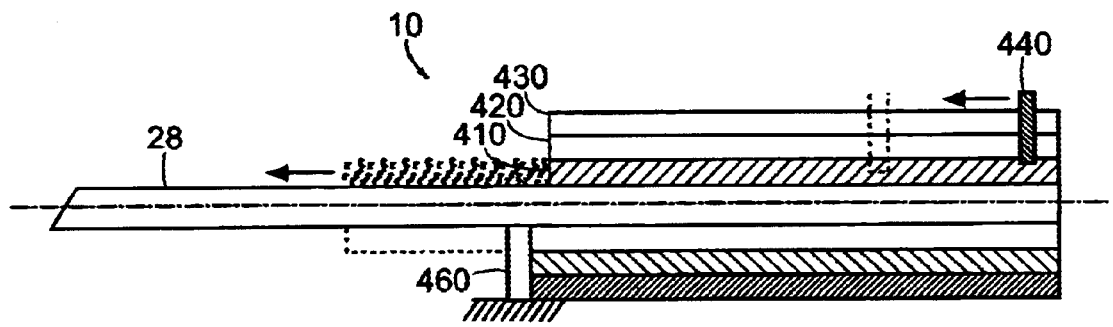
FIGS. 26C, 26D and 26F show longitudinal sectional views of the embodiment of FIG. 26A at various stages of operation.
Figure 26D:
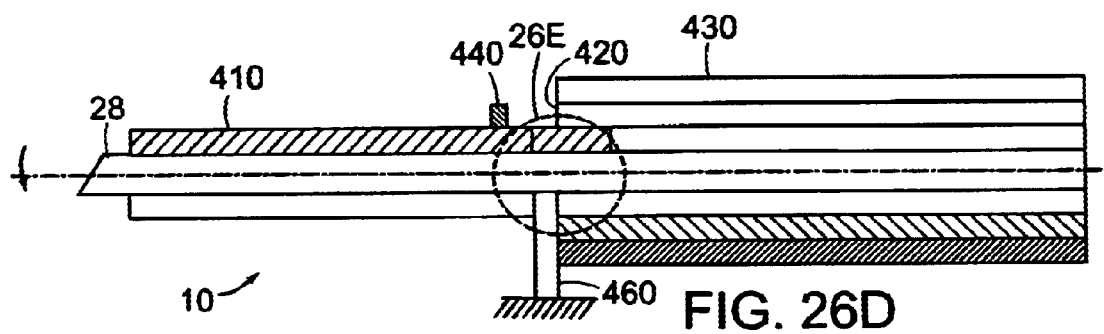
Figure 26E:
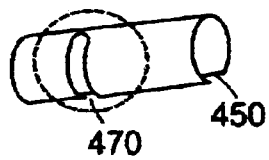
FIG. 26E shows a portion of a perspective view of component of the embodiment of FIG. 26A.
Figure 26F:
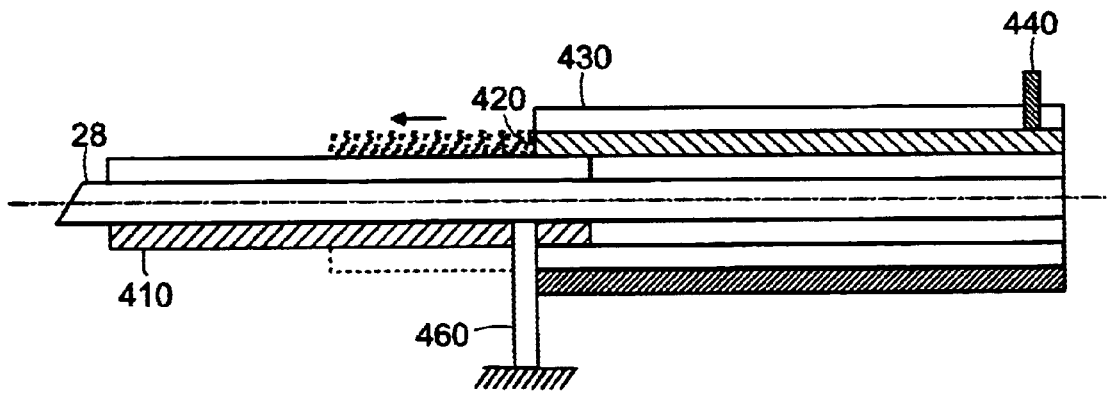

Coiled Spring:

FIG. 25 a coiled longitudinal spring 400 is fixed at its distal end to the needle 28 and at its proximal end to a cannula 88. The spring 400 is preferably made with Nitinol (NiTi). The spring 400 is introduced into the track of a patient in a relatively stretched, tense state. The spring 400 is then released by sliding the cannula 88 axially over the needle 28 in the distal direction. The spring thereby radially expands to dilate the track of a patient. Coiled springs may be used in combination with a mesh or braid, universal sheath 44 or any other suitable material.

Telescopic Dilators:

A set of sliding telescopic cannulas may be integrated into a single device similar in structure to a telescopic car antenna. The cannulas are introduced into a track of a patient sequentially over a needle to progressively dilate the track.

In FIGS. 22A–F, three telescopic cannulas 410, 420, and 430 are arranged over a guide needle 28. Each cannula has a longitudinal slot 450 to allow sliding of a moving index or pin 440 within, when the cannula is disposed at the proximal end of the dilation system 100, and to allow sliding of the cannulas from a retracted position through a fixed index 460 to attain an extended position in the track of the patient. Each cannula also possesses a radial slot 470 in an "L" shape at their proximal end to permit locking of the cannula in the extended position, by sliding the fixed index 460 therethrough.

To dilate the track of a patient, the smallest cannula 410 is first rotated to engage its longitudinal slot 450 over the fixed index 460, then a movable index 440 is used to push the cannula 410 within the track. The movable index 440 sliding through the longitudinal slots 450 of the outer cannulas 420 and 430. Finally, the cannula 410 is rotated back to engage radial slot 470 into the fixed index 460 and lock the cannula 410 in its extended position. This sequence is repeated with each of the other cannulas 420 and 430 as shown in the FIGS. 22A–E, until the desired track size is reached.

The movable index 440 may be actuated directly by the user, or by an actuation mechanism as described herein above such as rods connected to a dial in the handle (not shown).

Waistless Variable Dilation Balloons

In most cases, current balloons adequately dilate tissue medium whether it be surrounding a natural body lumen or a percutaneous track. However, there are two drawbacks associated with the use of current balloons. First, when dense scar tissue is encountered, higher pressure is utilized to overcome the resistance of the scar tissue, and formation of a waist in the balloon is observed. Second, current balloons work at a rated pressure and inflate to a fixed size. This means that, depending on the anatomy and the clinical setting, a set of several balloons has to be kept on hand to meet the varied needs.

The waistless variable dilation balloons described herein overcome these drawbacks by the use of a single device using a user actuation mechanism according the present invention.

Referring to FIGS. 27A–E, the waistless variable dilation balloons are composed of a tubular mesh 34 that surrounds a balloon 480 and is attached by adhesive, swaging or other means at its proximal end to the distal end of a cannula 88 disposed within the longitudinal groove 500 of the handle 24 and dial 26 of the dilation system 100. The mesh 34 is initially pulled tightly over the balloon 480 to achieve a low profile. The balloon 480 is attached at its proximal end to a catheter 43 which is disposed within the lumen of cannula 88 and the groove 500 and extends to the proximal end of handle 24. Catheter 43 carries fluid to the balloon from port 490 at proximal end of catheter 43. Catheter is fixedly attached to handle 24 along groove 500.

Figure 27A:
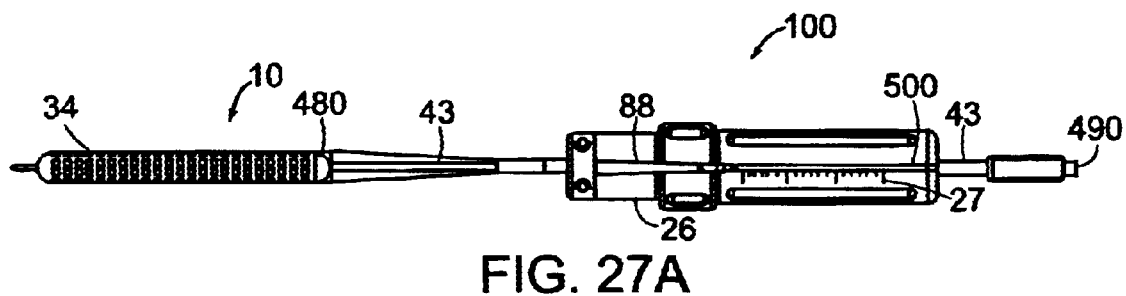
FIGS. 27A–27E shows various views of an embodiment of the dilation system of the invention with the top view in FIG. 27A; the side view in FIG. 27B; the perspective view in FIG. 27C; the front view in FIG. 27D; and the longitudinal cross sectional view in FIG. 27E.
Figure 27B:
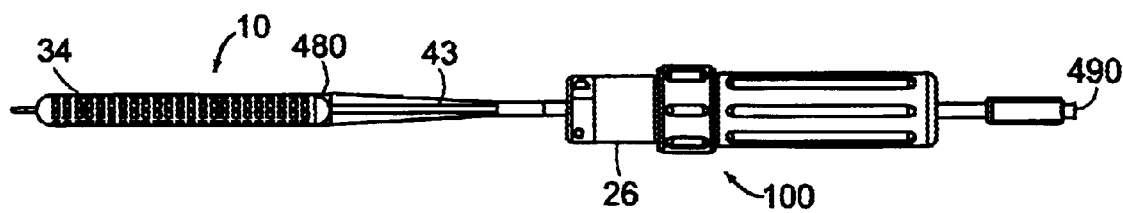
Figure 27C:
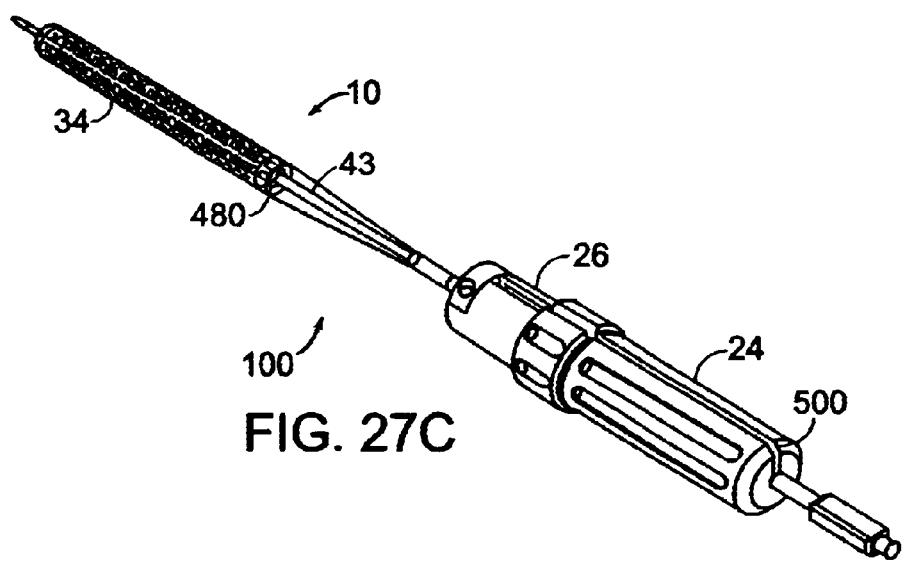
Figure 27D:
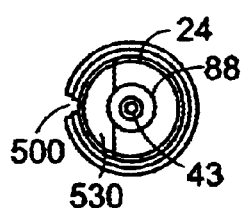

The cannula 88 fits into a longitudinal groove 500 extending from the circumference to the axis in the handle 24 and dial 26 shown in FIG. 27A, C and D, FIGS. 28A–D, FIGS. 29A–D. The cannula 88 has a disk 510 shown in FIGS. 30A–D which is fixedly connected to cannula 88 and locks into a transversal groove 520 positioned in the distal end of the dial 26 and covered by a cap 530, shown in FIGS. 27A–D and FIGS. 31A–D, that fits into a recess 540 shown in FIGS. 29A–D located on the half circumference of the proximal end of the dial 26 above the transversal groove 520. The cap 530 has a matching transversal groove 550 that fits atop the disk 510 of the cannula 88. Also the cap has two holes 560 for screwing, nailing or otherwise fixing the cap 530 on the dial 26 in the recess 540. The dial 26 also has two holes 570 located on each side of the transversal groove 520 for fixing the cap 530 on the dial 26.

The mesh 34 is fixedly connected to the catheter 43 at the distal end. The mesh 34 is retained and fixed to the distal end of the cannula 88. Shown in FIG. 30D and FIGS. 32A–D, the cannula 88 is further fitted at its proximal end with a tongue 580 that protrudes radially and stretches longitudinally along a portion of the length of the cannula for sliding within the longitudinal groove 500 of the handle 24 and dial 26. The tongue 580 locks rotational movements of the cannula 88 and avoid rotational distortions of the mesh 34. Further the tongue 580 serves as an index, with reference to the markings 27 graduated in units of French on the handle 24.

Figure 27E:
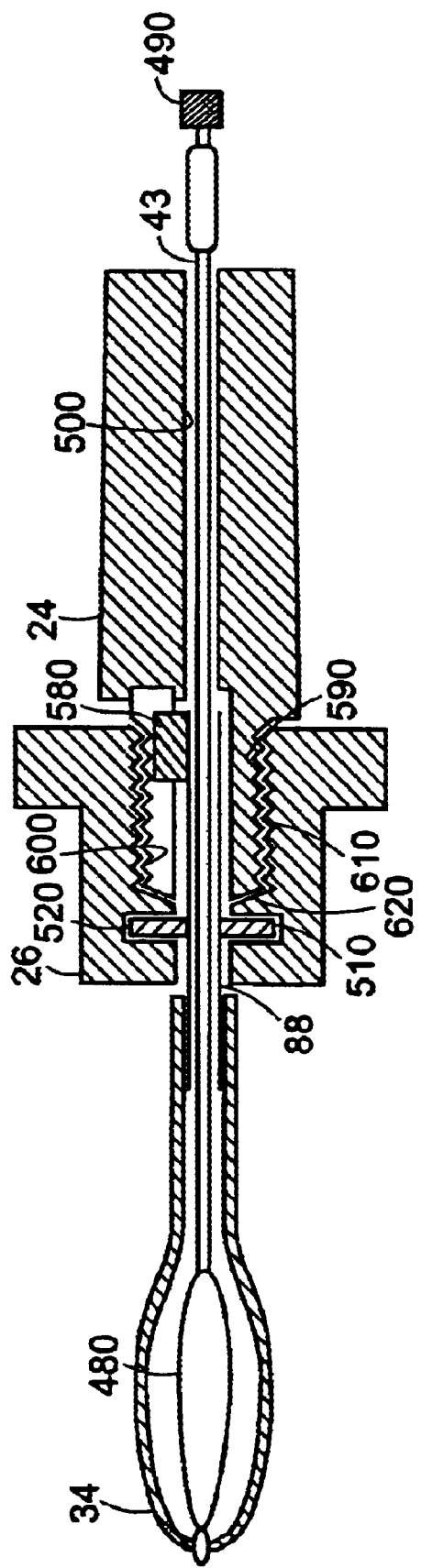
Figure 28A:
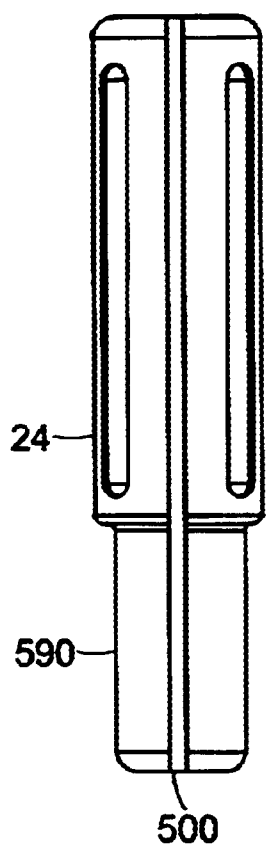
FIGS. 28A–28D show various views of a component of the handle of the dilation system shown in FIGS. 27A∫27E, with the top view in FIG. 28A; the side view in FIG. 28B; the perspective view in FIG. 28D; and the front view in FIG. 28D.
Figure 28B:
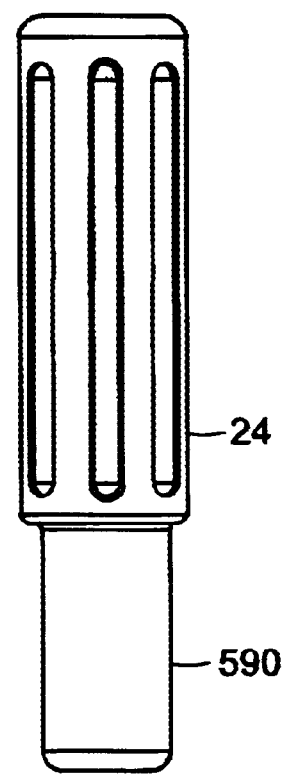
Figure 28C:
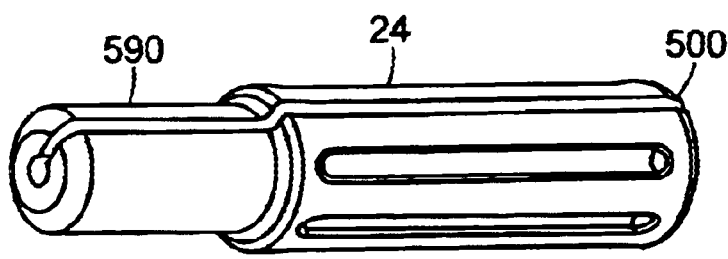
Figure 28D:
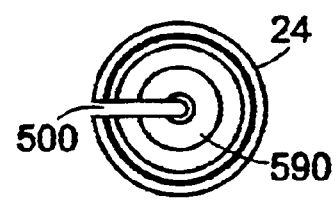
Figure 29A:
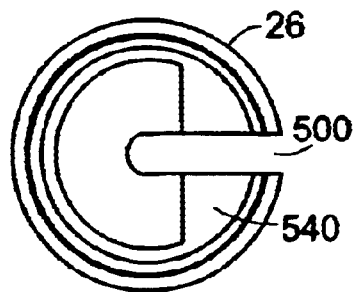
FIGS. 29A–29D show various views of another component of the handle of the dilation system shown in FIGS. 27A–27E, with the front view in FIG. 28A; the side view in FIG. 29B; the top view in FIG. 29C; and the perspective view in FIG. 29D.
Figure 29B:
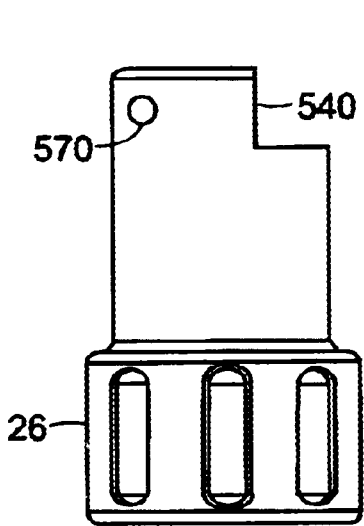
Figure 29C:
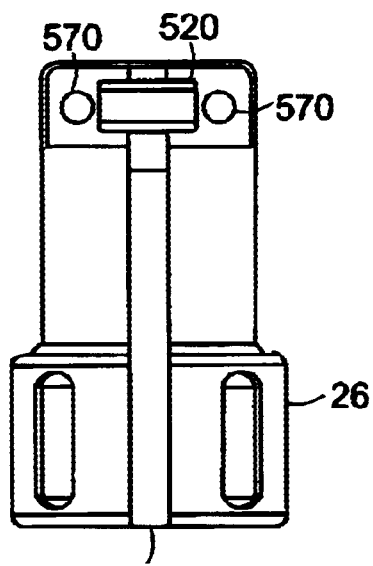
Figure 29D:
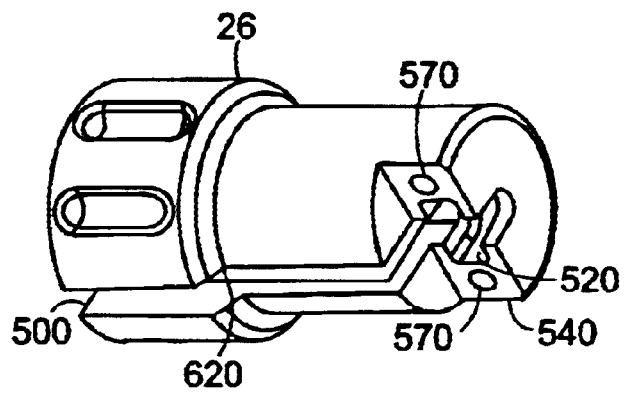
Figure 30A:
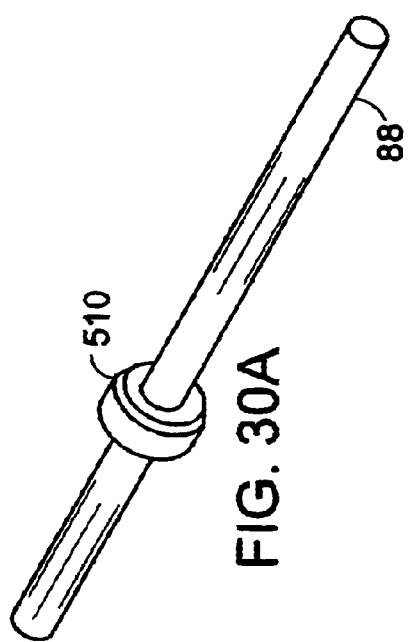
FIGS. 30A–30D show various views of another component of the dilation system shown in FIGS. 27A–27E with the perspective view in FIG. 30A; the side view in FIG. 30B; the front view in FIG. 30C; and another perspective view in FIG. 30D.
Figure 30B:
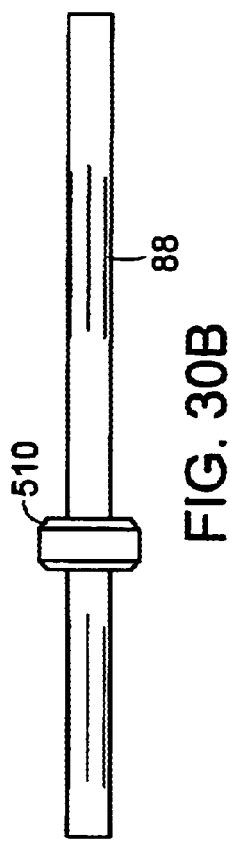
Figure 30C:
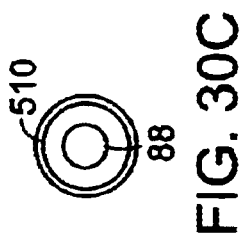
Figure 30D:
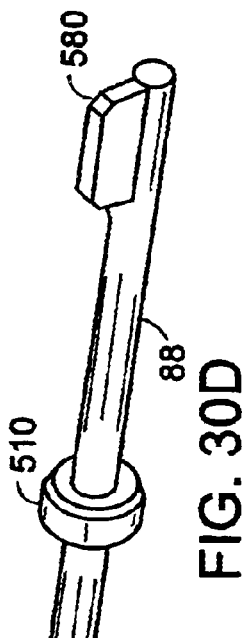
Figure 32A:
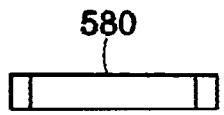
FIGS. 32A–32D shows various views of another component of the dilation system shown in FIGS. 27A–27E with the top view in FIG. 32A; the front view in FIG. 32B; the perspective view in FIG. 32C; and the side view in FIG. 32D.
Figure 32C:
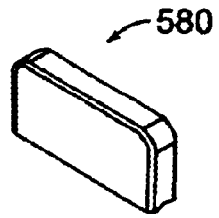
Figure 32B:
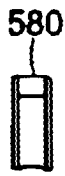
Figure 32D:
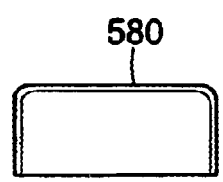
Figure 31A:
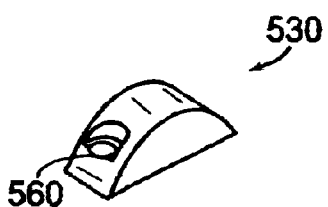
FIGS. 31A–31E show various views of another component of the dilation system shown in FIGS. 27A–27E with the perspective view in FIG. 3A; the side view in FIG. 31B; the top view in FIG. 31C; the front view in FIG. 31D; and the bottom view in FIG. 31E.
Figure 31C:
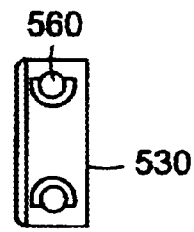
Figure 31B:
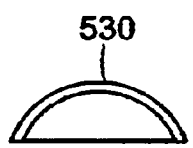
Figure 31D:
Figure 31E:
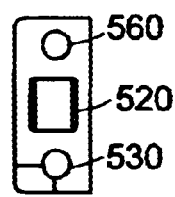

The distal end of the handle 24 has a circular protrusion 590 the surface of which is threaded 600 an fits into the thread 610 of an axial circular recess 620 of the dial 26 as shown in FIG. 27E.

Circular motion of the dial 26 advances distally or proximally the dial 26 along the protrusion 590 of the handle 24. Longitudinal motion of the dial 26 is transferred to cannula 88 by the disk 510 locked in groove 520 and 550. Longitudinal motion of the cannula 88 toward the distal end of dilation system 100 loosens the mesh 34 allowing the balloon 480 to expand upon entry of dilating fluid within the balloon 480 though the port 490 and catheter 43. Longitudinal motion of the cannula 88 toward the proximal end tightens the mesh 34 around the balloon 480 restricting expansion of the balloon 480.

Unlike standard balloons, where only radial forces are at play, the use of an overlaid mesh 34 in the waistless balloon compacts the balloon and creates dilation forces having both longitudinal and radial components. Higher pressure can now be applied to the balloons 480 and the mesh 34, maintaining the pressure throughout the length and circumference of the dilating element 10, forming minimal or no waist.

Alternatively the protrusion 590 and the recess 620 do not have their surfaces threaded as shown in FIGS. 28A–D. Relative longitudinal sliding motion of the dial 26 vis-a-vis the handle 24 transfers the motion to the cannula 88 which then dilates or loosens the mesh 34.

Referring to FIGS. 33A–B, optionally the dilation system may be fitted with a universal sheath 44, that is slid over the inflated balloon to maintain the track opening. The balloon 480 can then be deflated and the mesh 34 longitudinally tensed to remove the dilation system from the track.

FIGS. 34A–B shows an alternate embodiment of the waistless variable dilation balloon as a dilating element of the dilation systems of the invention. In this embodiment, the mesh 34 is fixed proximally to the distal end of the handle 24 and distally, to the distal end of the cannula 88 by a washer 72. The washer 72 locks relative longitudinal motions of the cannula 88 and the distal end of the mesh 34 but allows free rotational motions of the cannula 88 without imparting these rotational motions to the mesh 34 thus avoiding rotational distortion of the mesh.

The proximal end of the cannula 88 has a thread 78 which engage into a corresponding thread 77 in the handle 24. The proximal end of the cannula 88 is further fitted with a dial button 26 bearing an index 27 which when activated by the user, adopt a plurality of radial positions in reference with the marking indices 27 on the handle 24.

FIG. 34A shows the deflated state of the dilating element with the cannula 88 pushed distally. FIG. 34B shows an inflated state of the dilating element with the cannula pulled proximally. Waistless variable dilation balloons may also be made with the universal sheath 44 as covering for the balloons in place of the mesh 34.

Dilation Method with Forced Expansion:

Forced expansion may be carried out using a dial-a-size type actuation mechanism according to the present invention. These forced expansion methods force the track to open through a shearing type action similar to the use of conventional renal dilators, instead of the progressive radial expansion applied by the dilation systems described above. As opposed to the renal dilators, however, only one dilation system with a dilating element actuated by a dial-a-size actuation mechanism is needed to open the track to a desired size.

For example, a single malecot may be used as dilating element with the forced expansion methods. The malecot has the same configuration as, for example, that shown in FIG. 14A. The malecot is first introduced into the track, dilated, and then pulled out of the track to gradually dilate the entire length of a track. Other dilating elements described above can be used in a similar fashion.

Alternatively, a malecot, or other dilating element may be dilated outside of the body and then forced through the track opening. The desired diameter of dilation is adjusted before each introduction of the dilating element.

It will be apparent to those skilled in the art that various modifications and variations can be made in the dilation systems and methods of the present invention and in construction of the dilation systems without departing from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A dilation system for dilating a natural or created track of a body, the dilation system comprising:
    a dilating element for insertion into the track of the body, said dilating element comprising a balloon and a mesh or a braid overlaying the balloon, said mesh or braid being expandable along its length to any of a plurality of diameters; and
    an actuating mechanism integrally connected to said mesh or braid for restricting the radial expansion of said dilating element to any of the plurality of diameters, the actuating mechanism comprising a dial and a transmission mechanism, the transmission mechanism comprising at least one tubular member fixedly connected to a proximal end of the mesh or braid and including a disk for engagement in a circular groove in said dial, the transmission mechanism connected proximally to said dial and distally to said mesh or braid and transferring a longitudinal motion, rotational motion, or a combination thereof from said dial to said mesh or braid.

2. The dilation system of claim 1, wherein said dial further comprises indices.

3. The dilation system of claim 1, wherein said transmission mechanism comprises at least one tubular member selected from the group consisting of a cannula, a rod, a shaft, and a needle.

4. The dilation system of claim 1, wherein said transmission mechanism converts and transfers a rotational motion of said dial to said dilating element.

5. The dilation system of claim 1, wherein said transmission mechanism comprises a second tubular member fixedly connected to a distal end of the mesh or braid.

6. The dilation system of claim 1, further comprising a handle for housing a proximal portion of said actuating mechanism.

7. The dilation system of claim 6, further comprising the dial movably disposed over a distal portion of the handle and connected to said actuating mechanism.

8. A dilation system for dilating a natural or created track of a body, the dilation system comprising:

a dilating element for insertion into the track of the body, said dilating element comprising a balloon and a mesh or a braid overlaying the balloon, said mesh or braid being expandable along its length to any of a plurality of diameters; and an actuating mechanism integrally connected to said mesh or braid for restricting the radial expansion of said dilating element to any of the plurality of diameters, the actuating mechanism comprising a dial and a transmission mechanism, the transmission mechanism comprising at least one tubular member fixedly connected to a proximal end of the mesh or braid and including a tongue for engagement with a groove in a handle, the transmission mechanism connected proximally to said dial and distally to said mesh or braid and transferring a longitudinal motion, rotational motion, or a combination thereof from said dial to said mesh or braid.

9. The dilation system of claim 8, wherein said dial further comprises indices.

10. The dilation system of claim 8, wherein said transmission mechanism comprises at least one tubular member selected from the group consisting of a cannula, a rod, a shaft, and a needle.

11. The dilation system of claim 8, wherein said transmission mechanism converts and transfers a rotational motion of said dial to said dilating element.

12. The dilation system of claim 8, wherein said transmission mechanism comprises a tubular member fixedly connected to a distal end of the mesh or braid.

13. The dilation system of claim 8, further comprising the handle for housing a proximal portion of said actuating mechanism.

14. The dilation system of claim 13, further comprising a dial movably disposed over a distal portion of the handle and connected to said actuating mechanism.

* * * * *

UNITED STATES PATENT AND TRADEMARK OFFICE
CERTIFICATE OF CORRECTION

PATENT NO.    : 6,616,678 B2
DATED         : September 9, 2003
INVENTOR(S)   : Srinivas Nishtala et al.

It is certified that error appears in the above-identified patent and that said Letters Patent is hereby corrected as shown below:

<u>Column 24,</u>
Line 14, after "mechanism comprises a" insert -- second --

Signed and Sealed this

Twenty-seventh Day of July, 2004

JON W. DUDAS
*Acting Director of the United States Patent and Trademark Office*